(12) United States Patent
Bassaganya-Riera

(10) Patent No.: US 8,084,500 B2
(45) Date of Patent: *Dec. 27, 2011

(54) METHOD OF USING CATALPIC ACID TO TREAT DYSLIPIDEMIA

(75) Inventor: Josep Bassaganya-Riera, Blacksburg, VA (US)

(73) Assignee: Nutrition Therapeutics, Inc., Blacksburg, VA (US)

( * ) Notice: Subject to any disclaimer, the term of this patent is extended or adjusted under 35 U.S.C. 154(b) by 629 days.

This patent is subject to a terminal disclaimer.

(21) Appl. No.: 12/228,800

(22) Filed: Aug. 15, 2008

(65) Prior Publication Data

US 2009/0234008 A1    Sep. 17, 2009

Related U.S. Application Data

(63) Continuation-in-part of application No. 11/287,588, filed on Nov. 28, 2005, now Pat. No. 7,687,544.

(60) Provisional application No. 60/644,284, filed on Jan. 14, 2005.

(51) Int. Cl.
*A61K 31/20* (2006.01)

(52) U.S. Cl. ........................... 514/558; 514/560

(58) Field of Classification Search .................. 514/558, 514/560
See application file for complete search history.

(56) References Cited

U.S. PATENT DOCUMENTS

| | | | |
|---|---|---|---|
| 6,451,439 B2 | 9/2002 | Okamato | |
| 6,593,514 B1 | 7/2003 | Cahoon | |
| 7,560,442 B2 | 7/2009 | Susilo | |
| 7,687,544 B2 * | 3/2010 | Bassaganya-Riera | 514/588 |
| 7,834,058 B2 * | 11/2010 | Bassaganya-Riera | 514/558 |
| 2002/0045232 A1 | 4/2002 | Qiu | |
| 2003/0126640 A1 | 7/2003 | Cahoon | |

FOREIGN PATENT DOCUMENTS

| | | |
|---|---|---|
| EP | 1175901 A | 1/2002 |
| JP | 2002-265985 | 9/2002 |
| JP | 2002-176913 A | 6/2003 |

OTHER PUBLICATIONS

Bassaganya-Riera, J., K. Reynolds, et al (2004) *Gastroenterology* 127(3): 777-91. "Activation of PPAR gamma and delta by conjugated linoleic acid mediates protection from experimental inflammatory bowel disease".

Center for Disease Control (2004). National diabetes fact sheet: general information and national estimates on diabetes in the United States, 2003. Atlanta, U.S. Department of Health and Human Services, Centers for Disease Control and Prevention.

Chawla, A., W. A. Boisvert, et al. (2001) *Mol Cell* 7: 161-71. "A PPAR gamma-LXR-ABCA1 pathway in macrophages is involved in cholesterol efflux and atherogenesis".

Chinetti, G., S. Lestavel, et al. (2001) *Nature Medicine* 7: 53-8. "PPAR-Alpha and PPAR-gamma activators induce cholesterol removal from human macrophage foram cells through stimulation of the ABCA1 pathway".

Davidson, M. H., A. Armani, et al. (2007) *Am J Cardiol* 99: 3C-18C, "Safety considerations with fibrate therapy".

Ginsberg, H. N. (2003) *Am J Cardiol* 91(7A): 29E-39E. "Treatment for patients with the metabolic syndrome".

Guri, A. J., R. Hontecillas, et al. (2008) *J Nutr Biochem* 19: 216-28. "Loss of PPAR gamma in immune cells impairs the ability of abscisic acid to improve insulin sensitivity by suppressing monocyte chemoattractant protein-1 expression and macrophage infiltration into while adipose tissue".

Hellemans K., K. Kerckhofs, et al. (2007) *FEBS J* 274: 6094-105. "Peroxisome proliferator-activated receptor alpha-retinoid X receptor agonists induce beta-cell protection against palmitate toxicity".

Hossain, M. A., M. Tsujita, et al. (2008) *Cardiovasc Pharmacol* 51: 258-66. "Effects of fibrate drugs on expression of ABCA1 and HDL biogenesis in hepatocytes".

Hontecillas, R., M J. Wannemeulher, et al (2002) *J Nutr* 132: 2019-27. "Nutritional regulation of porcine bacterial-induced colitis by conjugated linoleic acid".

Knowler, W. C., R. F. Hamman, et al. (2005) *Diabetes* 54: 1150-6. "Prevention of type 2 diabetes with troglitazone in the Diabetes Prevention Program".

Remick, J., H. Weintraub, et al. (2008) *Cardiol Rev* 16: 129-41. "Fibrate therapy: an update".

Tsunoda, M., N. Kobayashi, et al. (2008) *Am J Physiol Endocrinol Metab* 294: E833-40. "A novel PPAr {alpha} agonist ameliorates insulin resistance in dogs fed a high-fat diet".

Walczak, R. & Tontonoz, P. (2002) *J Lipid Res* 43: 177-86. "PPARadigms and PPARadoxes: expanding roles for PPARgamma in the control of lipid metabolism".

Wang, Y. X., C. H. Lee, et al. (2003) *Cell* 113(2): 159-70. "Peroxisome-proliferator-activated receptor delta activates fat metabolism to prevent obesity".

\* cited by examiner

*Primary Examiner* — Kevin E Weddington
(74) *Attorney, Agent, or Firm* — Charles S. Sara, Esq.; Daniel A. Blasiole; DeWitt Ross & Stevens, S.C.

(57) ABSTRACT

A method of treating and preventing dyslipidemia, cardiovascular disease, type 2 diabetes, obesity and other diseases associated with the Metabolic Syndrome and of increasing the expression of genes that promote lipid oxidation in an animal, including mammals and humans, in which a therapeutically effective amount of catalpic acid is administered orally or parenterally to the animal.

16 Claims, 10 Drawing Sheets

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: PCR Primer

<400> SEQUENCE: 1
tggggatgaa gagggctgag                                                      20

<210> SEQ ID NO 2
<211> LENGTH: 19
<212> TYPE: DNA
<213> ORGANISM: Artificial Sequence
<220> FEATURE:
<223> OTHER INFORMATION: PCR Primer

<400> SEQUENCE: 2
ggggactgcc gttgtctgt                                                       19

<210> SEQ ID NO 3
<211> LENGTH: 20
<212> TYPE: DNA
<213> ORGANISM: Artificial Sequence
<220> FEATURE:
<223> OTHER INFORMATION: PCR Primer

<400> SEQUENCE: 3
acagtgacct ggcgctcttc                                                      20
```

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
tggtgtcctg gatggcttct                                              20

<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
caggcttgct gaacgtgaag                                              20

<210> SEQ ID NO 6
<211> LENGTH: 18
<212> TYPE: DNA
<213> ORGANISM: Artificial Sequence
<220> FEATURE:
<223> OTHER INFORMATION: PCR Primer

<400> SEQUENCE: 6
ggagcacctt ggcgaaca                                                18

<210> SEQ ID NO 7
<211> LENGTH: 20
<212> TYPE: DNA
<213> ORGANISM: Artificial Sequence
<220> FEATURE:
<223> OTHER INFORMATION: PCR Primer

<400> SEQUENCE: 7
tgggcaagtg ctaatggacc                                              20

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
ggccctggac tgtgtgaca                                               19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
cttcactgta agggcaggtg                                              20

<210> SEQ ID NO 10
<211> LENGTH: 20
<212> TYPE: DNA
<213> ORGANISM: Artificial Sequence
<220> FEATURE:
<223> OTHER INFORMATION: PCR Primer -continued

```
<400> SEQUENCE: 10
cttgagttgg gaatcagcag                                               20

<210> SEQ ID NO 11
<211> LENGTH: 19
<212> TYPE: DNA
<213> ORGANISM: Artificial Sequence
<220> FEATURE:
<223> OTHER INFORMATION: PCR Primer

<400> SEQUENCE: 11
cccaggcatt gctgacagg                                                19

<210> SEQ ID NO 12
<211> LENGTH: 20
<212> TYPE: DNA
<213> ORGANISM: Artificial Sequence
<220> FEATURE:
<223> OTHER INFORMATION: PCR Primer

<400> SEQUENCE: 12
tggaaggtgg acagtgaggc                                               20
```

METHOD OF USING CATALPIC ACID TO TREAT DYSLIPIDEMIA

CROSS-REFERENCE TO RELATED APPLICATIONS

This application is a continuation-in-part of U.S. patent application Ser. No. 11/287,588, filed Nov. 28, 2005 now U.S. Pat. No. 7,687,544 and claims priority under 35 U.S.C. §119 (e) to U.S. Provisional Application Ser. No. 60/644,284, filed Jan. 14, 2005, the entirety of which is incorporated herein.

FIELD OF THE INVENTION

The present invention is generally directed to a method of using catalpic acid to treat and prevent metabolic diseases and disorders in animals, including mammals and humans. More specifically, a method is provided using catalpic acid to normalize impaired glucose tolerance, prevent hyperglycemia and hyperinsulinemia, improve glucose tolerance and type 2 diabetes, attenuate the detrimental effects of high fat diets, minimize abdominal fat accumulation, treat and prevent dyslipidemia by increasing high-density lipoprotein levels and decreasing plasma triglyceride levels, and increase expression of genes involved in lipid oxidation.

CITED REFERENCES

A full bibliographic citation of the references cited in this application can be found in the section preceding the claims.

DESCRIPTION OF THE PRIOR ART

A need exists for novel methods of treating or preventing metabolic disorders such as the Metabolic Syndrome or Syndrome X. The Metabolic Syndrome constitutes a cluster of related, overlapping disorders derived from defects in the metabolism of macronutrients such as glucose and lipids. The disorders include obesity, type 2 diabetes, insulin resistance (hyperinsulinemia), dyslipidemia such as hyperlipidemia, cardiovascular disease, and hypertension (Ginsberg 2003). The dyslipidemia is characterized by hypertriglyceridemia, low high-density lipoprotein (HDL) cholesterol levels and elevated low density lipoprotein (LDL) cholesterol levels (Ginsberg 2003). Treating dyslipidemia reduces the risk of cardiovascular disease in patients with the Metabolic Syndrome (Ginsberg 2003). In western societies, the high prevalence of obesity results in several metabolic disorders such as type 2 diabetes, cardiovascular disease, hypertension, and hyperlipidemia, which are characterized as Metabolic Syndrome or Syndrome X (Wang et al. 2003).

The Metabolic Syndrome has an estimated age-adjusted US prevalence of 23.7% (Ginsberg 2003). According to estimates published in the National Diabetes Fact Sheet from the Centers for Disease Control and Prevention (CDC), the number of Americans afflicted by diabetes increased from 5.8 million in 1980 to 13.3 million in 2002, representing 6.3% of the population with 1 million newly diagnosed cases and $132 billion in medical expenses per year (CDC 2004).

Many treatments against the Metabolic Syndrome target the disease symptoms and not the cause. For instance, aspirin is recommended for its suppressive effect on platelet aggregation, and beta-blockers are utilized for treating diabetic hypertension and to reduce the mortality associated with cardiovascular disease. Novel treatments for insulin resistance include agonists of peroxisome proliferator-activated receptor (PPAR) gamma such as thiazolidinediones (TZDs), whereas statins and fibrates are utilized to favorably modify the blood lipid profiles and treat the dyslipidemia found in Metabolic Syndrome patients (Ginsberg 2003). However, questions have been raised regarding the safety of TZD-based treatments due to adverse cardiovascular (fluid retention and congestive heart failure) and liver (fatty liver) side effects. Therefore, there remains a need to identify novel and safer methods of preventing or treating the Metabolic Syndrome, dyslipidemia, cardiovascular disease, type 2 diabetes, obesity, and their complications, including nutritional methods that act upon molecular networks located in the interface between immunity, inflammation and metabolism.

Catalpic acid is a non-toxic, natural, orally active compound. Catalpic acid is naturally found in seeds of some ornamental trees, i.e., *Catalpa ovata* (Chinese Catalpa), *Catalpa speciosa* (Northern Catalpa), *Catalpa bungei*, or *Catalpa bigninioides*, representing 40 to 70 percent of the oil. The presence of catalpic acid in the seeds of catalpa trees is well-known in the field. Also, the capacity of triglyceride esters of catalpic acid to serve as drying oils in the fabrication of primers or adhesion or sealing compositions is well-known in the field. For instance, U.S. Pat. No. 6,451,439 to Okamoto teaches a method of effecting adhesion for sealing compositions. However, this method does not teach the use of catalpa oil or catalpic acid to treat or prevent metabolic disorders, such as dyslipidemia, cardiovascular disease, type 2 diabetes, obesity or the Metabolic Syndrome.

U.S. Pat. No. 6,593,514 to Cahoon teaches a method for the production of calendic acid, a fatty acid containing delta-8, 10, 12 conjugated double bonds and related fatty acids having a modification at the delta-9 position. While the patent lists catalpic acid in a long list of conjugated trienes, this method does not teach the use of catalpa oil or catalpic acid to treat and prevent metabolic disorders, such as dyslipidemia, cardiovascular disease, type 2 diabetes, obesity or the Metabolic Syndrome.

U.S. Patent Application 20030126640 to Cahoon teaches a method for preparing and using nucleic acid fragments encoding plant fatty acid modifying enzyme associated with conjugated double bond formation or functionally equivalent subfragments thereof. This method could be utilized to create transgenic plants producing altered lipid profiles. These altered lipid profiles could include catalpic acid and other conjugated trienes. However, this method does not teach the use of these conjugated trienes in general or catalpic acid in particular in the prevention and treatment of metabolic disorders, such as dyslipidemia, cardiovascular disease, type 2 diabetes, obesity or the Metabolic Syndrome.

U.S. Patent Application 20020045232 to Qiu teaches a method for large-scale production of conjugated fatty acids, especially conjugated linoleic and linolenic acids in plants. The invention relates to genes identified from *Calendula officinalis* coding for a conjugase and its related enzyme, a DELTA.12 desaturase, and utilization of them for large scale production of conjugated linoleic and linolenic acids in plants. The constructs containing these genes can be transferred to plants with different substrate profiles, which allows for the production of conjugated linoleic acids (18:2, DELTA.8, DELTA.10) and linolenic acids (DELTA.8, DELTA.10, DELTA.12) in plant seeds on a commercial scale. However, this method does not teach the use of conjugated linoleic or linolenic acids in general or catalpic acid in particular in the prevention and treatment of metabolic disorders, such as dyslipidemia, cardiovascular disease, type 2 diabetes, obesity or the Metabolic Syndrome.

It is therefore an object of the present invention to provide a method of treating and preventing type 2 diabetes and obesity of an animal, including mammals and humans, using catalpic acid.

It is still another object of the present invention to provide a method of treating and preventing the impaired glucose tolerance, the hyperglycemia, the hyperinsulinemia and the excessive abdominal fat accumulation found in type 2 diabetes and obesity by using catalpic acid.

It is still another object of the present invention to provide a method to ameliorate the detrimental metabolic changes associated with the consumption of a meal containing a high concentration of fat by using catalpic acid.

It is another object of the present invention to provide a method of treating and preventing the complications derived from insulin resistance, type 2 diabetes and obesity such as the ischemic diabetic foot syndrome, hypertension, nephropathy, neuropathy, retinopathy, polycystic ovaries, and cardiovascular disease, including coronary heart disease, endothelial dysfunction and myocardial infarction by using catalpic acid.

It is also an object of the present invention to provide a method of treating and preventing dyslipidemia by increasing HDL and decreasing triglycerides in the plasma of an animal, including mammals and humans, using catalpic acid.

It is another object of the present invention to increase expression of genes involved in lipid oxidation, such as PPAR alpha, PPAR delta, SCD, and ECH, using catalpic acid.

SUMMARY OF THE INVENTION

In response to the above-described needs, the present invention provides a method of treating and preventing dyslipidemia, cardiovascular disease, insulin resistance, type 2 diabetes and obesity and increasing the expression of genes that promote lipid oxidation in an animal, including mammals and humans, in need thereof. The method comprises administering a therapeutically effective amount of a compound selected from the group consisting of catalpic acid, esters thereof, pharmaceutically-suitable salts thereof, metabolites thereof, and combinations thereof.

The present invention is also directed to a method of increasing PPAR alpha and PPAR alpha responsive genes in white adipose tissue and/or PPAR delta in the pancreas, comprising administering an amount of a compound selected from the group consisting of catalpic acid, esters thereof, pharmaceutically-suitable salts thereof, metabolites thereof, and combinations thereof, wherein the amount is effective to increase PPAR alpha in white adipose tissue and/or PPAR delta in the pancreas.

In addition, the present invention provides a compound or composition for treating dyslipidemia, cardiovascular disease, type 2 diabetes and abdominal obesity signs comprising an effective amount of a compound selected from the group consisting of catalpic acid, non-toxic salts thereof, active esters thereof, structural lipids containing catalpic acid, methyl and ethyl esters thereof, active metabolites thereof and other active chemical derivatives thereof and mixtures thereof, in combination with a pharmaceutically-acceptable carrier.

The compound may be administered to the animal in a single dose or in multiple doses. This method utilizes the natural qualities of catalpic acid to treat and prevent dyslipidemia, cardiovascular disease, type 2 diabetes and obesity in an animal, including mammals and humans. Specifically, an amount effective to normalize impaired glucose tolerance, prevent hyperglycemia, prevent hyperinsulinemia, and minimize abdominal fat accumulation is administered. While any of the catalpic acid forms may be used, in a preferred embodiment, the free acid form of catalpic acid is used.

In a preferred embodiment of the present invention, the catalpic acid compound is administered orally to the animal. The catalpic acid compound may also be administered parenterally, via injection or rectally. The catalpic acid compound may be administered alone or in combination with a pharmaceutically suitable carrier or excipient.

In another embodiment of the present invention, a therapeutically effective amount of the catalpic acid compound is administered to an animal in combination with a nutritional food supplement. Such supplements include but are not limited to infant formulas, children products, geriatric formulas, milk, cheese, kefir, cereal bars, weight management formulas, energy bars, other human foods, functional foods, and animal feed. Catalpic acid may also be administered in combination with other active ingredients such as vitamins or other fatty acids.

The effective amount of the catalpic acid compound depends on the needs of the animal. For instance, in one embodiment, an amount effective to increase HDL and decrease blood triglycerides in an animal is provided.

The formulations of catalpic acid disclosed in the present invention may be conveniently presented in unit dosage form and may be prepared by any methods well known in the art of pharmacy or nutrition. Possible formulations include but are not limited to capsules, cachets, tablets, boluses or lozenges, each containing a predetermined amount of catalpic acid.

There are many advantages to the method of the present invention. For instance, there is no upper limit on the amount of catalpic acid that may be administered to an animal in need thereof. Further, the method of the present invention may be administered to animals, including mammals and humans, of all ages and health. For instance, vulnerable populations such as metabolic syndrome patients, the elderly, obese, diabetic, sick or very young can benefit from the present invention, as can healthy individuals with no history of chronic disease. In addition, the method of the present invention may be administered in a variety of ways, thereby providing a versatile and efficient means of preventing metabolic disorders in a mammal.

The objects and advantages of the invention will appear more fully from the following detailed description of the preferred embodiment of the invention made in conjunction with the accompanying drawings.

DETAILED DESCRIPTION OF THE INVENTION

Definitions

Figure 1A:
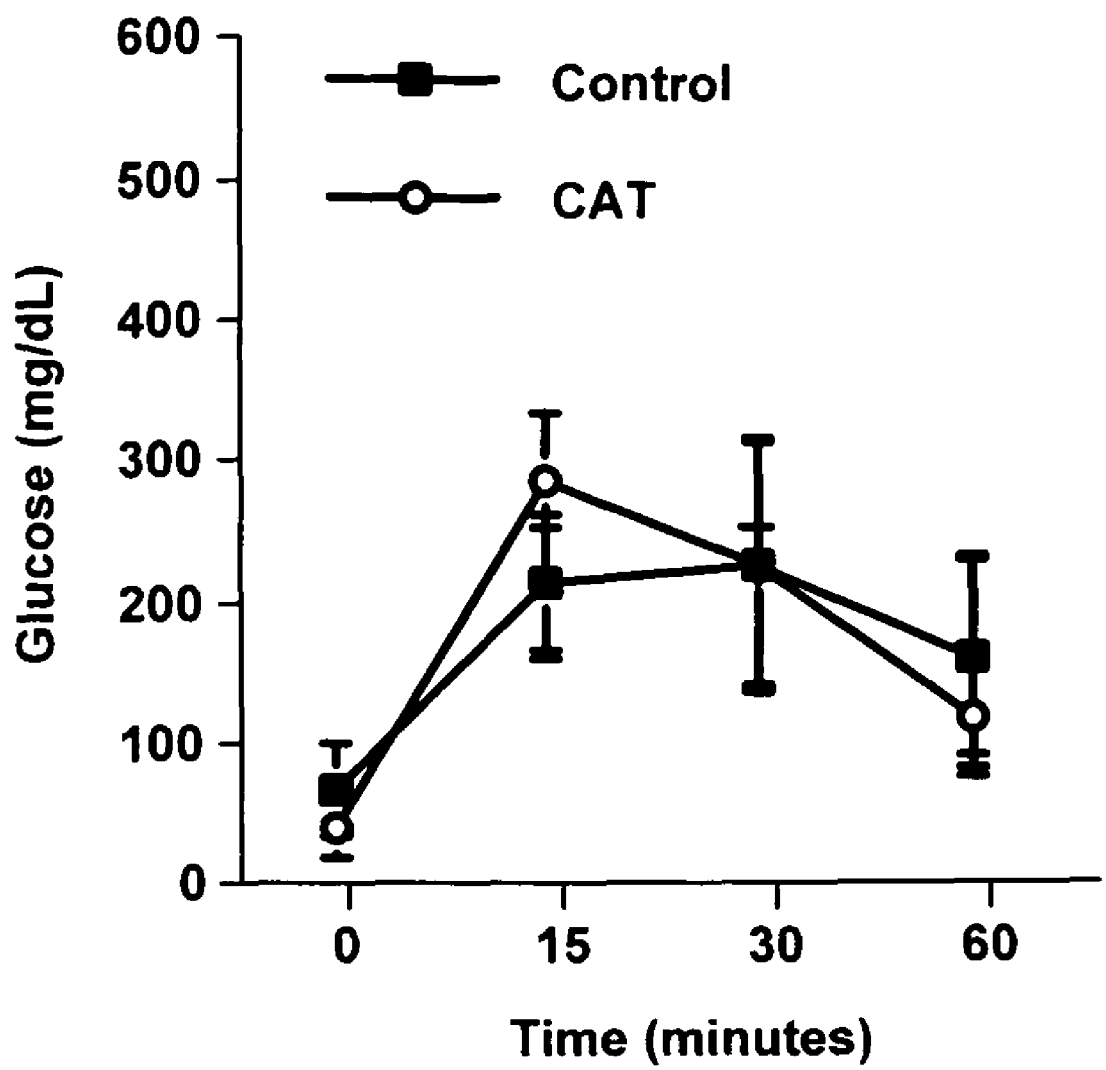
FIG. 1A is a graph illustrating the effect of catalpic acid on blood glucose concentrations during a glucose tolerance test in mice fed regular diets from Experiment 1.

Unless otherwise stated, the following definitions are used throughout the present application:

ANOVA: analysis of variance. Arithmetic process for partitioning the overall variation in data sets into specific components based on sources of variation. It has been used to determine whether numerical differences between treatment groups are statistically significant.

Adipogenesis: the process by which new adipocytes or fat storage cells are generated.

Allele: one of a number of viable DNA codings of the same gene.

Conjugate triene: a polyunsaturated fatty acid containing three double bonds separated by two single bonds.

Db/db mice: term used to define a type of mouse that lacks both alleles of the long isoform of the leptin receptor. This deficiency results in mice that overeat, are obese, develop dyslipidemia, and have a high predisposition to developing type 2 diabetes. Reference is made to Experiment 2 (infra.) for further discussions on db/db mice.

Glycemia: concentration of glucose in blood.

HDL: high-density lipoprotein. Lipoproteins are lipid-protein emulsions that carry lipids through the bloodstream. HDL is a high-density lipoprotein that occurs in a density range well known in the art. HDL primarily carries cholesterol through the bloodstream. In a process known as reverse cholesterol transport, HDL transports cholesterol from peripheral tissues to the liver, where it is excreted as cholesterol or metabolized into bile acids and excreted. Thus, high levels of HDL cholesterol are considered beneficial because they represent a pool of cholesterol that is targeted for excretion from the body rather than remaining in the bloodstream.

Hypercholesterolemia: increased concentrations of cholesterol in blood beyond the normal ranges.

Hyperglycemia: increased concentrations of glucose in blood beyond the normal ranges.

Hyperinsulinemia: increased concentrations of insulin in blood beyond the normal ranges.

Hyperlipidemia: increased concentrations of lipids (fats) in blood beyond the normal ranges.

Insulinemia: concentration of insulin in blood.

Insulin resistance: inability of tissues to respond to insulin and take up glucose from the blood.

Peroxisome proliferator-activated receptors (PPAR): proteins that are transcription factors involved in regulating glucose and lipid homeostasis and immune function. There are three isoforms (types) of PPARs: alpha, gamma, and delta. The alpha and delta isoforms are involved in burning (oxidizing) lipids, whereas the gamma isoform is involved in storing lipids.

Substantially pure: having a purity of at least 90% by weight, preferably at least 95% by weight such as at least 98%, 99% or about 100% by weight.

Triglyceride (TG): lipid molecule consisting in three acyl chains appended to a glycerol backbone via an ester linkage. High triglyceride levels in the bloodstream are linked with such diseases as diabetes and the Metabolic Syndrome.

Type 2 diabetes or Non-insulin dependent Diabetes Mellitus: term referring to a common type of diabetes caused by an unresponsiveness of cells to the actions of insulin. If the cells do not respond to insulin, they are unable to take up glucose from blood, which results in glucotoxicity. In addition, the cells are deprived from the energy derived from glucose oxidation.

Catalpic Acid

The term as used herein refers to a conjugated linolenic acid isomer containing trans-9, trans-11, cis-13 double bonds in the $C_{18}$ carbon chain, its non-toxic salts, active esters, active isomers, active metabolites, structural lipids containing catalpic acid, and mixtures thereof. Catalpic acid is found in the seed oil of *Catalpa ovata*, *Catalpa speciosa*, *Catalpa bungei* and *Catalpa bignininoides*. Catalpic acid constitutes approximately 60% of the oil of the catalpa seed. Active esters include, for example, alkyl esters having from 1 to 6 carbon atoms in the alkyl group, as well as mono-, di- and tri-glycerides, and mixtures thereof. Active isomers of catalpic acid include geometrical isomers. Non-toxic salts include sodium, potassium, calcium and magnesium salts.

The catalpic acid may be a substantially pure single chemical compound or a mixture of one or more catalpic acid compounds as defined above. The term "substantially pure" means having a purity of at least 90% by weight, preferably at least 95% by weight such as at least 98%, 99% or about 100% by weight. The catalpic acid may be in the form of an extract obtainable or obtained from Catalpa seed oil, either directly or following one or more steps of purification.

The catalpic acid used in the described methods may be in a free acid form or bound chemically through ester linkages. In its natural form, catalpic acid is heat stable. Catalpic acid may be used in its natural oil state or in a dried and powdered form. Further, the free acid form of catalpic acid may be converted into a non-toxic salt, such as sodium, potassium or calcium salts, by reacting chemically equivalent amounts of the free acid form with an alkali hydroxide at a basic pH.

Administration

In the course of the method of the present invention, a therapeutically effective amount of catalpic acid compound is administered to an animal, including mammals and humans, in many ways. While in the preferred embodiment, the catalpic acid compound is administered orally or parenterally, other forms of administration such as through medical compounds or aerosols are also contemplated.

For oral administration, the effective amount of catalpic acid may be administered in, for example, a solid, semi-solid, liquid or gas state. Specific examples include tablet, capsule, powder, granule, solution, suspension, syrup, and elixir agents. However, the catalpic acid compound is not limited to these forms.

To formulate the catalpic acid of the present invention into tablets, capsules, powders, granules, solutions or suspensions, the catalpic acid compound is preferably mixed with a binder, a disintegrating agent and/or a lubricant. If necessary, the resultant composition may be mixed with a diluent, a buffer, an infiltrating agent, a preservative and/or a flavor, using known methods. Examples of the binder include crystalline cellulose, cellulose derivatives, cornstarch, and gelatin. Examples of the disintegrating agent include cornstarch, potato starch, and sodium carboxymethylcellulose. Examples of the lubricant include talc and magnesium stearate. Further, additives, which have been conventionally used, such as lactose and mannitol, may also be used.

For parenteral administration, the catalpic acid compound of the present invention may be administered rectally or by injection. For rectal administration, a suppository may be used. The suppository may be prepared by mixing the catalpic acid of the present invention with a pharmaceutically suitable excipient that melts at body temperature but remains solid at room temperature. Examples include but are not limited to cacao butter, carbon wax or polyethylene glycol. The resulting composition may be molded into any desired form using methods known to the field.

For administration by injection, the catalpic acid compound of the present invention may be injected hypodermically, intracutaneously, intravenously or intramuscularly. Medicinal drugs for such injection may be prepared by dissolving, suspending or emulsifying the catalpic acid of the invention into an aqueous or non-aqueous solvent such as vegetable oil, glyceride of synthetic resin acid, ester of higher fatty acid, or propylene glycol by a known method. If desired, additives such as a solubilizing agent, an osmoregulating agent, an emulsifier, a stabilizer, or a preservative, which has been conventionally used may also be added.

For formulating the catalpic acid of the present invention into suspensions, syrups or elixirs, a pharmaceutically suitable solvent may be used.

The catalpic acid compound of the present invention may also be used together with an additional compound having other pharmaceutically suitable activity to prepare a medicinal drug.

The catalpic acid of the present invention may also be administered in the form of an aerosol or inhalant prepared by charging the catalpic acid in the form of a liquid or fine powder, together with a gaseous or liquid spraying agent and, if necessary, a known auxiliary agent such as an inflating agent, into a non-pressurized container such as an aerosol container or a nebulizer. A pressurized gas of, for example, dichlorofluoromethane, propane or nitrogen may be used as the spraying agent.

Catalpic acid may be administered to an animal, including mammals and humans, in need thereof as a pharmaceutical or veterinary composition, such as tablets, capsules, solutions or emulsions. In a preferred embodiment of the invention, the free acid form of catalpic acid is administered. However, administration of other forms of catalpic acid, including but not limited to esters thereof, pharmaceutically-suitable salts thereof, metabolites thereof, and combinations thereof, in a single dose or a multiple dose, are also contemplated by the present invention.

Catalpic acid may also be administered to an animal in need thereof as a nutritional additive, either as a food or nutraceutical supplement.

The terms "preventing or treating," "treating or ameliorating" and similar terms used herein, include prophylaxis and full or partial treatment. The terms may also include reducing symptoms, ameliorating symptoms, reducing the severity of symptoms, reducing the incidence of disease, or any other change in the condition of the patient, which improves the therapeutic outcome.

The catalpic acid is preferably used and/or administered in the form of a composition. Suitable compositions are, preferably, a pharmaceutical composition, a foodstuff or a food supplement. These compositions provide a convenient form in which to deliver the catalpic acid. Compositions of the invention may comprise an antioxidant in an amount effective to increase the stability of the catalpic acid with respect to oxidation.

The amount of catalpic acid that is administered in the method of the invention or that is for administration in the use of the invention is preferably from about 0.001 g to about 20 g (more preferably 0.1 g to 10 g, such as 0.5 g to 5 g) of catalpic acid or derivative thereof per day. Suitable compositions can be formulated accordingly.

A preferred composition according to the invention is a foodstuff. Food products (the term includes animal feed) preferably contain a fat phase, wherein the fat phase contains catalpic acid. The foodstuffs are optionally used as a blend with a complementary fat. For example, the blend may comprise 0.3-95% weight, preferably 2-80% weight, most preferably 5-40% weight of catalpic acid and 99.7-5% weight, preferably 98-20% weight, most preferably 95-60% weight of a complementary fat, for example selected from: cocoa butter, cocoa butter equivalents, palm oil or fractions thereof, palm kernel oil or fractions thereof, interesterified mixtures of said fats or fractions thereof, or liquid oils, selected from: sunflower oil, high oleic sunflower oil, soybean oil, rapeseed oil, cottonseed oil, fish oil, safflower oil, high oleic safflower oil, maize oil and medium chain triglyceride oils. Examples of suitable foodstuffs include those selected from the group consisting of margarines, fat continuous or water continuous or bicontinuous spreads, fat reduced spreads, confectionery products such as chocolate or chocolate coatings or chocolate fillings or bakery fillings, ice creams, ice cream coatings, ice cream inclusions, dressings, mayonnaises, cheeses, cream alternatives, dry soups, drinks, cereal bars, sauces, snack bars, dairy products, clinical nutrition products and infant formulations.

Other examples of compositions are pharmaceutical compositions, such as in the form of tablets, pills, capsules, caplets, multi-particulates including: granules, beads, pellets and micro-encapsulated particles; powders, elixirs, syrups, suspensions and solutions. Pharmaceutical compositions will comprise a pharmaceutically acceptable diluent or carrier. Pharmaceutical compositions are preferably adapted for administration parenterally, e.g., orally. Orally administrable compositions may be in solid or liquid form and may take the form of tablets, powders, suspensions and syrups. Optionally, the compositions comprise one or more flavoring and/or coloring agents.

Pharmaceutically acceptable carriers suitable for use in such compositions are well known in the art of pharmacy. The compositions of the invention may contain 0.1-99% by weight of catalpic acid. The compositions of the invention are generally prepared in unit dosage form. Preferably the unit dosage of catalpic acid is from 1 mg to 1000 mg (more preferably from 100 mg to 750 mg). The excipients used in the preparation of these compositions are the excipients known in the art.

Further examples of product forms for the composition are food supplements, such as in the form of a soft gel or a hard capsule comprising an encapsulating material selected from the group consisting of gelatin, starch, modified starch, starch derivatives such as glucose, sucrose, lactose and fructose. The encapsulating material may optionally contain cross-linking or polymerizing agents, stabilizers, antioxidants, light absorbing agents for protecting light-sensitive fills, preservatives and the like. Preferably, the unit dosage of catalpic acid in the food supplements is from 1 mg to 1000 mg (more preferably from 100 mg to 750 mg).

Dose

The method of the present invention administers a therapeutically effective amount of catalpic acid compound to an animal in need thereof. The effective amount of catalpic acid depends on the form of catalpic acid compound administered, the duration of the administration, the route of administration, e.g., oral or parenteral, the age of the animal and the condition of the animal.

For instance, an amount of catalpic acid effective to enhance treat and prevent type 2 diabetes and obesity in an animal ranges from 10-10,000 mg/kg/day. A preferred effective amount of catalpic acid is 100 to 5,000 mg/kg/day, with a more preferred dose being 10 to 100 mg/kg/day. An effective amount of approximately 35 to 40 mg/kg/day of catalpic acid is also envisioned by the method of the present invention, with 38 mg/kg/day the preferred dose. The upper limit of the effective amount to be administered is not critical, as catalpic acid is relatively non-toxic as long as the recipient's diet contains the necessary essential fatty acids.

The effective amount of catalpic acid is most effective in treating and preventing metabolic disorders such as type 2 diabetes and obesity of an animal when administered to an animal for periods ranging from about 7 to 100 days, with a preferred period of 15 to 50 days, and a most preferred period of 32 to 42 days.

When the effective amount of the catalpic acid compound of the present invention is administered in a nutritional, medical or veterinary composition, the preferred dose ranges from about 0.01 to 2.0% wt/wt to the food or nutraceutical product.

Preparation of Catalpic Acid

Solvent extraction methods are recommended to obtain good oil yields. Before solvent extraction, seeds are steam-heated to reduce enzymatic hydrolysis and improve processing. After heating, seeds of catalpa beans are finely ground and used in a solvent extraction. Regular liquid solvents such as hexane require soaking the seeds multiple times for up to 12 to 20 hours with stirring, filtering, and solvent evaporation. Alternatively, catalpic acid-enriched catalpa oil may be generated by $CO_2$ super critical extraction in methods known to the art.

Because the oil is more susceptible to oxidative processes when released from the seed, extraction is preferably performed under a nitrogen blanket to prevent contact with the air. Additionally, the oil is nitrogen-purged and stored with one or various antioxidants in the dark at 4° C. or at −20° C. for longer-term storage. Oil from catalpa seeds is expressed during this process in an amount by weight of 10% of the weight of the seeds.

The following non-limiting examples illustrate the invention and do not limit its scope in any way. In the examples and throughout this specification, all percentages, parts and ratios are by weight unless indicated otherwise.

The practice of the present invention is further illustrated by the following experiments, which were conducted.

EXPERIMENTS

Experiment 1

Objective

Experiment 1 was designed to determine the effect of catalpic acid on the development of obesity and type 2 diabetes induced by high fat diets. Specifically, we investigated whether catalpic acid was able to normalize impaired glucose tolerance, prevent hyperglycemia and hyperinsulinemia and attenuate abdominal fat accumulation in mice fed high fat diets.

Methods

In Western countries the Metabolic Syndrome or Syndrome X (i.e., diabetes, obesity, cardiovascular disease, hypertension and hyperlipidemia) is on a steady rise. The development of nutrition-based therapeutic or preventive interventions using orally active, natural compounds is not only timely but also urgently needed. A total of forty-seven C57BL6 mice were used in experiment 1. Twenty-five mice were fed a control diet and twenty-three mice were fed a diet supplemented with catalpic acid (0.6 g catalpic acid/100 g food). For the first 32 days of the experiment all diets contained 7% fat, 0.02% total cholesterol, and they obtained 14.5% of calories from fat by replacing catalpic acid with linoleic acid (wt/wt basis) in the control diet. See Table 1.

TABLE 1

Composition of the Regular Diets[1].

| Ingredient | Control Diet | Catalpic Diet |
|---|---|---|
| Casein | 200 | 200 |
| L-Cystine | 3 | 3 |
| Corn Starch | 397.486 | 397.486 |
| Maltodextrin | 132 | 132 |
| Sucrose | 100 | 100 |
| Cellulose | 50 | 50 |
| Mineral Mix (AIN-93)[2] | 35 | 35 |
| Vitamin Mix (AIN-93)[3] | 10 | 10 |
| Choline Bitartrate | 2.5 | 2.5 |
| Tert-butylhydroquinone[4] | 0.014 | 0.014 |
| Soybean oil | 60 | 60 |
| Linoleic acid | 10 | — |
| Catalpa oil | — | 10 |

[1]Provides approximately 7% fat and 0.02% total cholesterol and it obtains 14.5% of calories from fat.
[2]Supplied per kg of vitamin mix: 3 g nicotinic acid, 1.6 g calcium pantotenate, 0.7 g pyridoxine HCl, 0.6 g Thiamin HCl, 0.6 g riboflavin, 0.2 g folic acid, 0.02 g D-biotin, 2.5 g vitamin $B_{12}$ (0.1% in mannitol), 15 g DL-alpha tocopheryl acetate (500 IU/g), 0.8 g vitamin A palmitate (500,000 IU/g), 0.2 g vitamin $D_3$ (cholecalciferol, 500,000 IU/g), 0.075 g vitamin K (phylloquinone), and 974.705 g sucrose.
[3]Supplied per kg of mineral mix: 357 g calcium carbonate, 196 g potassium phosphate monobasic, 70.78 g potassium citrate, 74 g sodium chloride, 46.6 g potassium sulfate, 24.3 g magnesium oxide, 6.06 g ferric citrate, 1.65 g zinc carbonate, 0.63 g manganese carbonate, 0.31 g cupric carbonate, 0.01 g potassium iodate, 0.01025 g sodium selenate, 0.00795 g ammonium paramolybdate, 1.45 g sodium meta-silicate, 0.275 g chromium potassium sulfate, 0.0174 g lithium chloride, 0.0815 g boric acid, 0.0635 g sodium fluoride, 0.0318 g nickel carbonate, hydroxide, tetrahydrate, 0.0066 g ammonium vanadate, and 220.716 g sucrose.
[4]Antioxidant.

These diets are defined as regular diets and were formulated to be isocaloric between treatment groups. On day 32 of the experiment, twenty mice within each group were fed high fat diets containing 19.6% fat, 0.2% total cholesterol that obtained 40.1% of calories from fat by replacing catalpic acid with lard (wt/wt basis) in the control high fat diet. See Table 2.

TABLE 2

Composition of the High Fat Diets[1].

| Ingredient | Control Diet | Catalpic Diet |
|---|---|---|
| Casein | 232 | 232 |
| L-Cystine | 3.0 | 3.0 |
| DL-Methionine | 3.5 | 3.5 |
| Corn Starch | 137 | 137 |
| Maltodextrin | 150 | 150 |
| Sucrose | 162.595 | 162.595 |
| Cellulose | 50 | 50 |
| Cholesterol | 1.9 | 1.9 |
| Mineral Mix (AIN-93)[2] | 40.60 | 40.60 |
| Calcium phosphate dibasic | 4.64 | 4.64 |
| Vitamin Mix (AIN-93)[3] | 16.24 | 16.24 |
| Choline Bitartrate | 5 | 5 |
| Tert-butylhydroquinone[4] | 0.02 | 0.02 |
| Vitamin K, phylloquinone | 0.005 | 0.005 |
| Soybean oil | 30 | 30 |

TABLE 2-continued

Composition of the High Fat Diets[1].

| Ingredient | Control Diet | Catalpic Diet |
|---|---|---|
| Lard | 163.5 | 153.5 |
| Catalpa oil | — | 10 |

[1]Provides approximately 19.6% fat and 0.2% total cholesterol and it obtains 40.1% of kilocalories (Kcal) from fat (4.4 Kcal/g). Kcal density is approximately 16% higher than typical AIN-93G-based diets.
[2]Supplied per kg of vitamin mix: 3 g nicotinic acid, 1.6 g calcium pantotenate, 0.7 g pyridoxine HCl, 0.6 g Thiamin HCl, 0.6 g riboflavin, 0.2 g folic acid, 0.02 g D-biotin, 2.5 g vitamin $B_{12}$ (0.1% in mannitol), 15 g DL-alpha tocopheryl acetate (500 IU/g), 0.8 g vitamin A palmitate (500,000 IU/g), 0.2 g vitamin $D_3$ (cholecalciferol, 500,000 IU/g), 0.075 g vitamin K (phylloquinone), and 974.705 g sucrose.
[3]Supplied per kg of mineral mix: 357 g calcium carbonate, 196 g potassium phosphate monobasic, 70.78 g potassium citrate, 74 g sodium chloride, 46.6 g potassium sulfate, 24.3 g magnesium oxide, 6.06 g ferric citrate, 1.65 g zinc carbonate, 0.63 g manganous carbonate, 0.31 g cupric carbonate, 0.01 g potassium iodate, 0.01025 g sodium selenate, 0.00795 g ammonium paramolybdate, 1.45 g sodium meta-silicate, 0.275 g chromium potassium sulfate, 0.0174 g lithium chloride, 0.0815 g boric acid, 0.0635 fluoride, 0.0318 g nickel carbonate, hydroxide, tetrahydrate, 0.0066 g ammonium vanadate, and 220.716 g sucrose.
[4]Antioxidant.

The high fat diets were also formulated to be isocaloric between treatment groups. The remaining mice within each group (n=5) were fed the regular diets. On day 78 of the experiment, mice were killed, and blood was collected and immediately analyzed for fasting glucose concentrations by using the Accu-Check Instant Plus System (Roche Diagnostics Corporation, Indianapolis, Ind.) or stored for subsequent analysis of insulin and lipid concentrations in plasma. Abdominal white adipose tissue and interscapular brown adipose tissue were collected, weighed and stored at −80° C. for RNA analyses. Liver, lungs, kidneys, pancreas and heart were examined for macroscopic abnormalities (gross lesions), fixed in phosphate-buffered formalin (10%) and processed for histological evaluation. All specimens were generally labeled with the following information: 1) mouse number; 2) date collected; 3) experiment number; 4) type of solvent; and 5) tissue type.

Glucose Tolerance Tests

A glucose tolerance test was conducted on day 78 of the experiment. Animals were fasted overnight (14 hours). Mice were injected intraperitoneally with D-glucose (1 g/kg body weight) and blood samples were collected via the tail vein prior to the injection (time 0) and at 15, 30 and 60 minutes following the injection.

Determination of Serum Insulin Concentrations.

Serum insulin concentrations were determined by using commercially available enzyme-linked immunosorbent assay kits (Linco Research, St. Charles, Mo.).

Statistics

Data were analyzed by ANOVA. The ANOVA was performed by using the general linear model procedure of SAS (SAS Institute Inc., Cary, N.C.) as previously described (Bassaganya-Riera et al. 2004). Differences with probability value (P<0.05) were considered significant.

Results

Figure 1B:
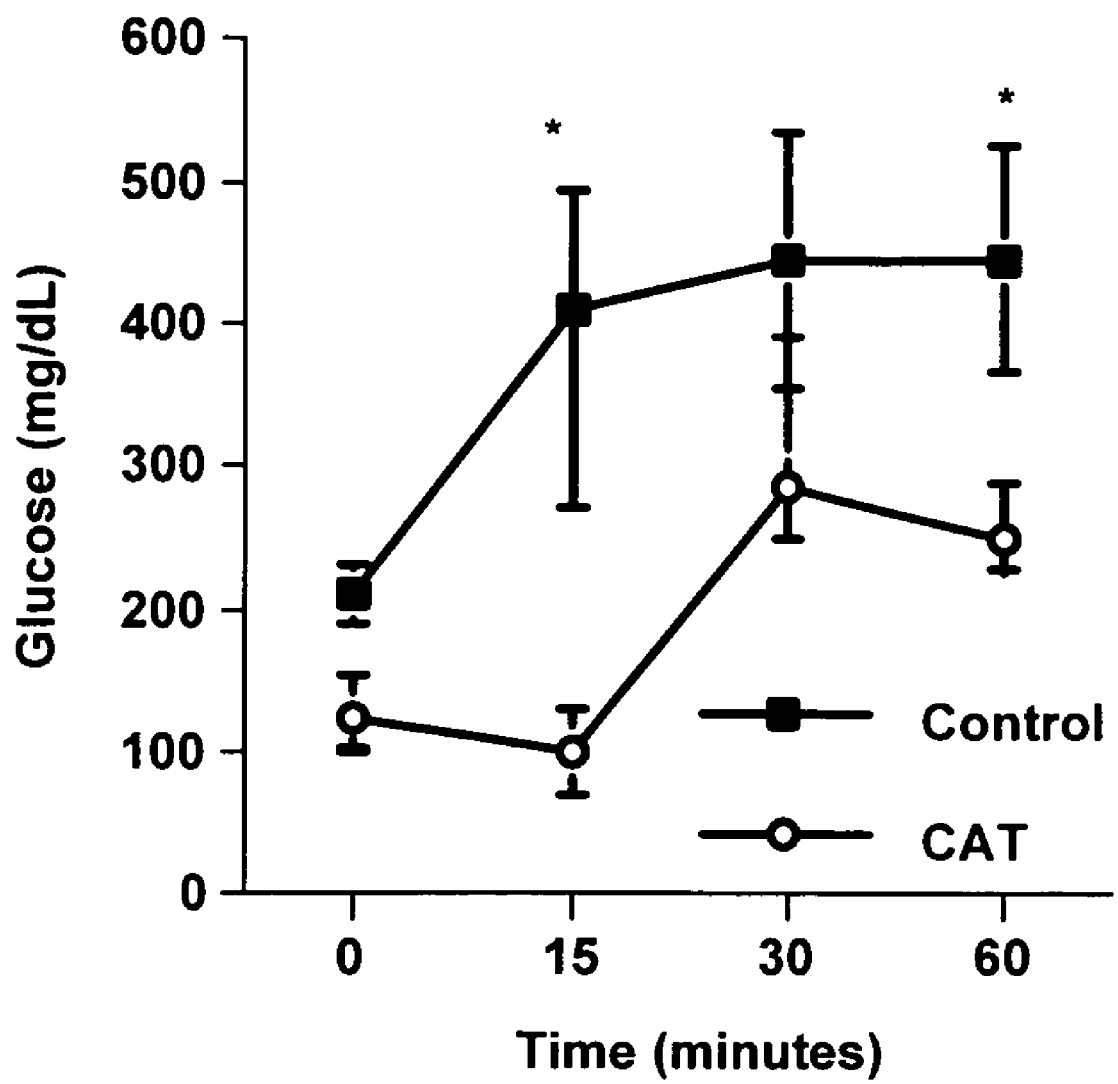
FIG. 1B is a graph illustrating the effect of catalpic acid on blood glucose concentrations during a glucose tolerance test in mice fed high fat diets from Experiment 1.

FIG. 1A illustrates the effect of catalpic acid on blood glucose concentrations during a glucose tolerance test in mice fed regular diets from Experiment 1. Mice were fed either a control diet (filled squares) or a diet supplemented with catalpic acid (1 g/100 g; open rubies). FIG. 1B illustrates the effect of catalpic acid on blood glucose concentrations during a glucose tolerance test in mice fed high fat diets from Experiment 1. Mice were fed either a high fat control diet (filled squares) or a high fat diet supplemented with catalpic acid (1 g/100 g; open rubies). Statistically significant differences (P<0.05) between treatments attributed to the main effects of the diet (*) are indicated.

Excessive abdominal fat accumulation and insulin resistance are key characteristics that typify the Metabolic Syndrome. The glucose tolerance tests are standard methods for evaluating glucose homeostasis in vivo. By using the glucose tolerance test, we discovered that glucose tolerance was not different between the two groups fed regular diets, which did not develop a diabetic phenotype (FIG. 1A). However, the ability of mice fed a control high fat diet to normalize impaired glucose tolerance was significantly impaired when compared to those fed the high fat diets supplemented with catalpic acid (FIG. 1B).

Furthermore, mice fed the control high fat diet were markedly more hyperglycemic and hyperinsulinemic than mice fed high fat diets supplemented with catalpic acid or mice fed regular diets. Reference is made to Table 3.

TABLE 3

Weight of abdominal white adipose tissue and interscapular brown adipose tissue and plasma fasting glucose and insulin concentrations in mice fed control or catalpic acid (CAT)-supplemented regular and high fat diets[1].

| | Regular Diets | | High Fat Diets | | | ANOVA P |
|---|---|---|---|---|---|---|
| Item | Control | CAT | Control | CAT | SEM[2] | value |
| White adipose tissue, g | 0.865[b] | 0.751[b] | 1.478[a] | 0.607[b] | 0.06 | 0.0001 |
| Brown adipose tissue, g | 0.130 | 0.169 | 0.129 | 0.105 | 0.008 | 0.08 |
| Glucose (mg/dL) | 153.8[b] | 146.20[b] | 301.30[a] | 205.43[b] | 11.3 | 0.0001 |
| Insulin (ng/mL) | 0.932[b] | 0.960[b] | 2.254[a] | 0.730[b] | 0.23 | 0.01 |

[1]Least squares means values in a row for a particular tissue with different superscripts are significantly different (P < 0.05).
[2]Pooled standard error of the least square means.

Thus, catalpic acid-supplementation prevents or ameliorates the development of hyperglycemia, attenuates the hyperinsulinemia and normalizes impaired glucose tolerance in mice fed high fat diets (Table 3). These findings are clinically significant in the prevention and treatment of type 2 diabetes, the Metabolic Syndrome and their complications (e.g., cardiovascular disease, stroke, retinopathy, nephropathy and amputations).

The hyperglycemia and hyperinsulinemia observed in mice fed control high fat diets correlated with increased abdominal white adipose tissue deposition (Table 3). However, no differences in brown adipose tissue weights were observed between groups. The decreased abdominal adiposity observed in mice fed high fat diets supplemented with catalpic acid when compared with mice fed the control diet could be caused by either suppressed adipogenesis or increased fatty acid consumption. Because fatty liver or enlarged viscera were not observed in mice fed catalpic acid-supplemented diets, the decreased abdominal obesity is unlikely to be caused by decreased adipogenesis and it may be due to increased fatty acid consumption. All of which, suggests that catalpic acid could be utilized in the treatment and prevention of insulin resistance, abdominal obesity and the Metabolic Syndrome.

Experiment 2

Objective

The data in Experiment 1 demonstrated that dietary catalpic acid-supplementation for 78 days had a positive effect on glucose tolerance, insulin resistance and abdominal adiposity. The goal of this study was to investigate whether dietary catalpic acid-supplementation for 30 days ameliorated or prevented impaired glucose tolerance, insulin resistance and abdominal adiposity in type 2 diabetic mice.

Methods

Mice were purchased from Harlan (Indianapolis, Ind.). Following an acclimation period of 5 days on regular rodent chow they were fed purified, high fat diets that represented a modification of the AIN-93G rodent diet in which the nutritional requirements, including those for polyunsaturated fatty acids (PUFA), were met or exceeded. See Table 4.

TABLE 4

Composition of the High Fat Diets in Experiment 2[1].

| Ingredient (g/kg) | Control Diet | CAT Diet |
|---|---|---|
| Casein | 232 | 232 |
| L-Cystine | 3.0 | 3.0 |
| DL-Methionine | 3.5 | 3.5 |
| Corn Starch | 137 | 137 |
| Maltodextrin | 150 | 150 |
| Sucrose | 162.58 | 162.58 |
| Cellulose | 50 | 50 |
| Cholesterol | 1.9 | 1.9 |
| Mineral Mix (AIN-93)[2] | 40.60 | 40.60 |
| Calcium phosphate dibasic | 4.64 | 4.64 |
| Vitamin Mix (AIN-93)[3] | 16.24 | 16.24 |
| Choline Bitartrate[4] | 5 | 5 |
| Tert-butylhydroquinone[5] | 0.04 | 0.04 |
| Soybean oil | 30 | 30 |
| Lard | 153.5 | 153.5 |
| Soybean oil | 10 | — |
| Catalpic oil | — | 10 |

[1]Provides approximately 19.6% fat, 0.2% total cholesterol and 4.4 kilocalories/g (kcal/g) it obtains 40% kcal from fat. Kcal density is approximately 16% higher than typical AIN-93G-based diets.
[2]Supplied per kg of vitamin mix: 3 g nicotinic acid, 1.6 g calcium pantotenate, 0.7 g pyridoxine HCl, 0.6 g Thiamin HCl, 0.6 g riboflavin, 0.2 g folic acid, 0.02 g D-biotin, 2.5 g vitamin $B_{12}$ (0.1% in mannitol), 15 g DL-alpha tocopheryl acetate (500 IU/g), 0.8 g vitamin A palmitate (500,000 IU/g), 0.2 g vitamin $D_3$ (cholecalciferol, 500,000 IU/g), 0.075 g vitamin K (phylloquinone), and 974.705 g sucrose.
[3]Supplied per kg of mineral mix: 357 g calcium carbonate, 196 g potassium phosphate monobasic, 70.78 g potassium citrate, 74 g sodium chloride, 46.6 g potassium sulfate, 24.3 g magnesium oxide, 6.06 g ferric citrate, 1.65 g zinc carbonate, 0.63 g manganous carbonate, 0.31 g cupric carbonate, 0.01 g potassium iodate, 0.01025 g sodium selenate, 0.00795 g ammonium paramolybdate, 1.45 g sodium meta-silicate, 0.275 g chromium potassium sulfate, 0.0174 g lithium chloride, 0.0815 g boric acid, 0.0635 g sodium fluoride, 0.0318 g nickel carbonate, hydroxide, tetrahydrate, 0.0066 g ammonium vanadate, and 220.716 g sucrose.
[4]The choline bitartrate concentrations have been increased from 2.5 g/kg in regular AIN-93G diets to 5 g/kg due to increased kcal density of high fat diets.
[5]Antioxidant.

Stock fatty acid solutions, e.g., soybean oil or catalpic acid were kept at −20° C. and nitrogen-purged every time that the bottles were opened. All the experimental diets contained the same amount of energy (isocaloric) and protein (isonitrogenous). To maintain the diets isocalorically, catalpic acid replaced soybean oil in the catalpic acid diet. We utilized male, db/db [BKS.Cg-+$Lepr^{db}$/+$Lepr^{db}$/OlaHsd (type 2 Diabetic)] mice (n=20) weighing 19.86 g on day 1 of the study. The db/db mice lack the long isoform of leptin receptor and represent a well-established model of type 2 Diabetes and are often utilized to determine the pre-clinical efficacy of antidiabetic drugs. Half of the mice were fed a control and the other half a catalpic acid-supplemented diet (1 g catalpa oil/100 g diet).

Assessment of Type 2 Diabetes

All mice were determined normoglycemic (210 mg/dl glucose or lower) and of similar body weights prior to assignment to experimental treatments. Mice were weighed on a daily basis and examined for clinical signs of disease by blinded observers. Water and feed intake were assessed on a daily basis. Fasting (12 h) glucose and insulin concentrations were determined on days 0, 7, 15, 21 and 28, of the study. Briefly, blood was collected via the caudal vein and placed onto capillary blood collection tubes. Insulin concentrations were determined by using a commercially available insulin enzyme-linked immunosorbent assay (ELISA) (Linco Research, St Charles, Mo.) per manufacturer's instructions. Mice were administered a glucose tolerance test and euthanized by $CO_2$ narcosis on day 28 of the study. For the glucose tolerance test, animals were fasted overnight (12 hours), injected intraperitoneally with D-glucose (2 g/kg body weight) and blood samples were collected via the caudal vein prior to the injection (time 0) and at 15, 30, 60, 90, 120 and 180 minutes following the injection to determine the effect of CAT on the kinetics of glucose normalization.

Statistics

Data were analyzed by ANOVA. The ANOVA was performed by using the general linear model procedure of SAS (SAS Institute Inc., Cary, N.C.) as previously described (Bassaganya-Riera et al. 2004). Data were analyzed as a completely randomized design. Differences with probability value ($P<0.05$) were considered significant.

Results

Fasting Glucose and Insulin Concentrations

Figure 2A:
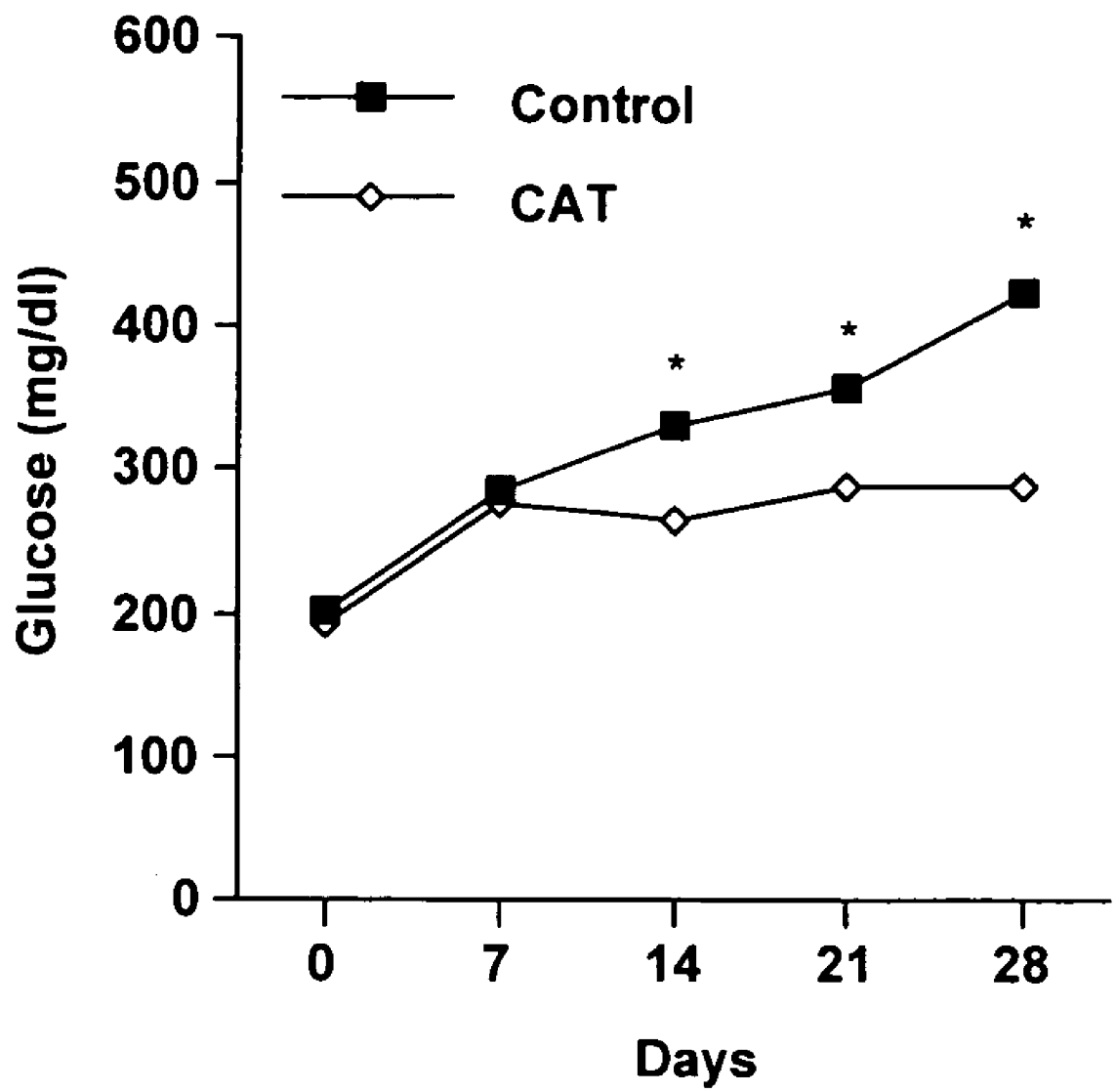
FIG. 2A is a graph illustrating the effect of dietary catalpic acid-supplementation on fasting plasma glucose concentrations on days 0, 7, 14, 21 and 28 of Experiment 2.
Figure 2B:
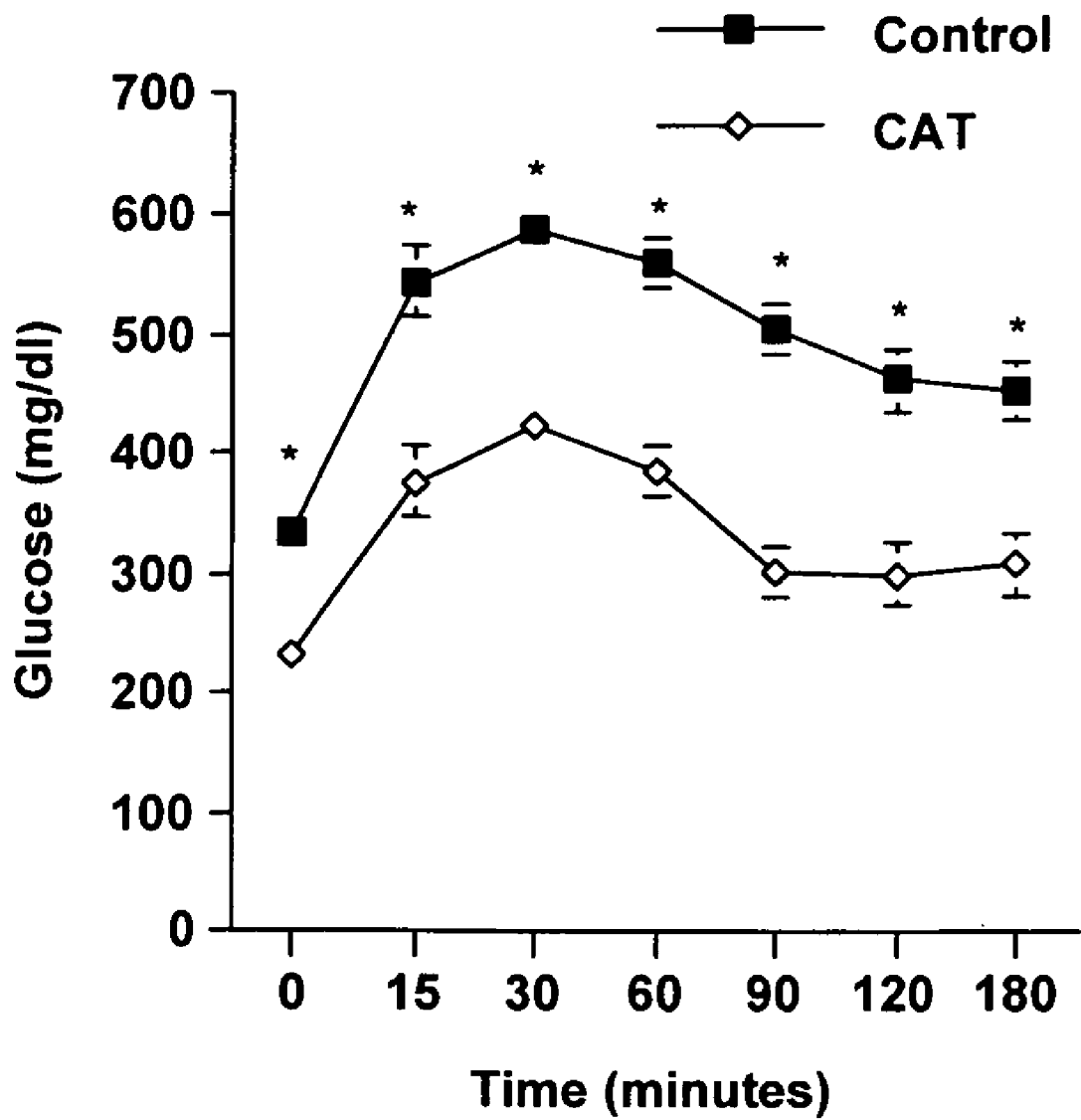
FIG. 2B is a graph illustrating the effect of dietary catalpic acid-supplementation on plasma glucose concentrations during a glucose tolerance test from Experiment 2.

FIG. 2A illustrates the effect of dietary catalpic acid-supplementation on fasting plasma glucose concentrations on days 0, 7, 14, 21 and 28 of Experiment 2. Db/db mice were fed either a high fat control diet (filled squares) or a high fat diet supplemented with catalpic acid (1 g/100 g; open rubies). Statistically significant differences ($P<0.05$) between treatments attributed to the main effects of the diet (*) are indicated. FIG. 2B illustrates the effect of dietary catalpic acid-supplementation on plasma glucose concentrations during a glucose tolerance test from Experiment 2. Blood was collected at 0, 15, 30, 60, 90, 120 and 180 minutes following the intraperitoneal glucose challenge (2 g/Kg body weight). Db/db mice fed either a high fat control diet (filled squares) or a high fat diet supplemented with catalpic acid (1 g/100 g; open rubies). Statistically significant differences ($P<0.05$) between treatments attributed to the main effects of the diet (*) are indicated.

To determine the effect of catalpic acid on insulin sensitivity and glucose homeostasis, we examined fasting plasma glucose and insulin concentrations on days 0, 7, 14, 21 and 28 of the study. We found that the levels of plasma glucose were significantly ($P<0.05$) lower in mice fed high fat, catalpic acid-supplemented diets than in those fed high fat control diets on days 14, 21 and 28 (FIG. 2A). On day 28 of the experiment the glucose concentrations in db/db mice fed the control high fat diet corresponded to a diabetic phenotype (425 mg/dl) whereas dietary catalpic acid-supplementation maintained mice in a pre-diabetic stage (290 mg/dl) (FIG. 2B).

Figure 3:
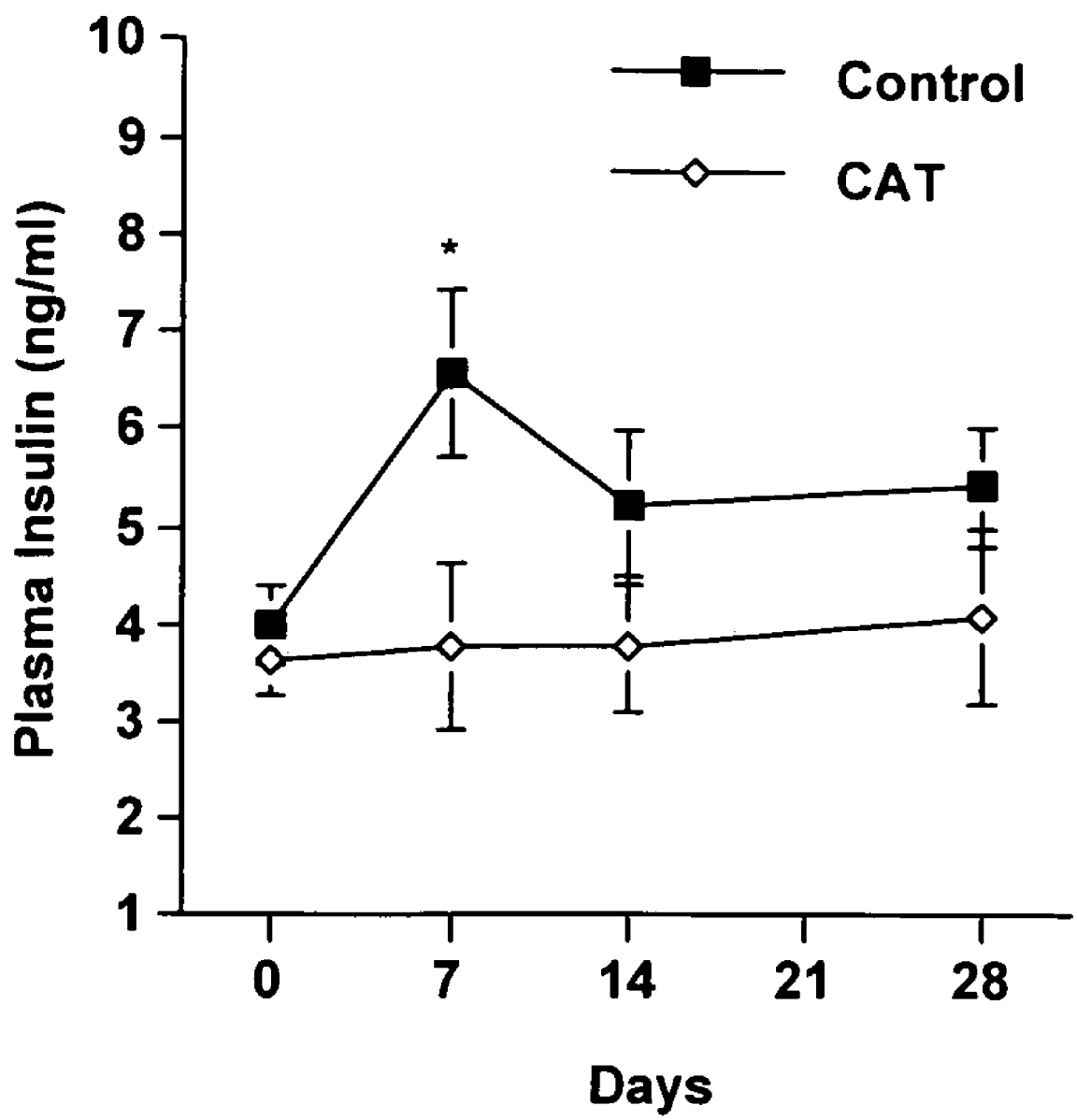
FIG. 3 is a graph illustrating the effect of dietary catalpic acid-supplementation on fasting plasma insulin concentrations on days 0, 7, 14 and 28 of Experiment 2.

These differences in plasma glucose levels observed on day 28 of the study in db/db mice correlated with plasma insulin concentrations as shown in FIG. 3. FIG. 3 illustrates the effect of dietary catalpic acid-supplementation on fasting plasma insulin concentrations on days 0, 7, 14 and 28 of Experiment 2. Db/db mice fed either a high fat control diet (filled squares) or a high fat diet supplemented with catalpic acid (1 g/100 g; open rubies). Statistically significant differences (P<0.05) between treatments attributed to the main effects of the diet (*) are indicated. More specifically, plasma insulin concentrations in db/db mice fed the catalpic acid-supplemented diets remained at basal levels (i.e., lower than 4 ng/ml). However, db/db mice fed the control diet overproduced insulin on day 7 (6.54 ng/ml) and the insulin levels in mice fed the control diet remained higher throughout the study (FIG. 3).

Glucose Tolerance Test

To determine whether dietary catalpic acid would enhance the glucose normalizing ability of mice fed high fat diets, we performed an intraperitoneal glucose challenge and evaluated the kinetics of plasma glucose at 0, 15, 30, 60, 90, 120 and 180 minutes following the glucose injection. We found that the glucose normalizing ability of mice fed catalpic acid-supplemented diets was greater than in mice fed control diets in all time points examined as shown in FIG. 2B.

Body Weight, Feed Intake and White Adipose Tissue (WAT) Weight

Figure 4A:
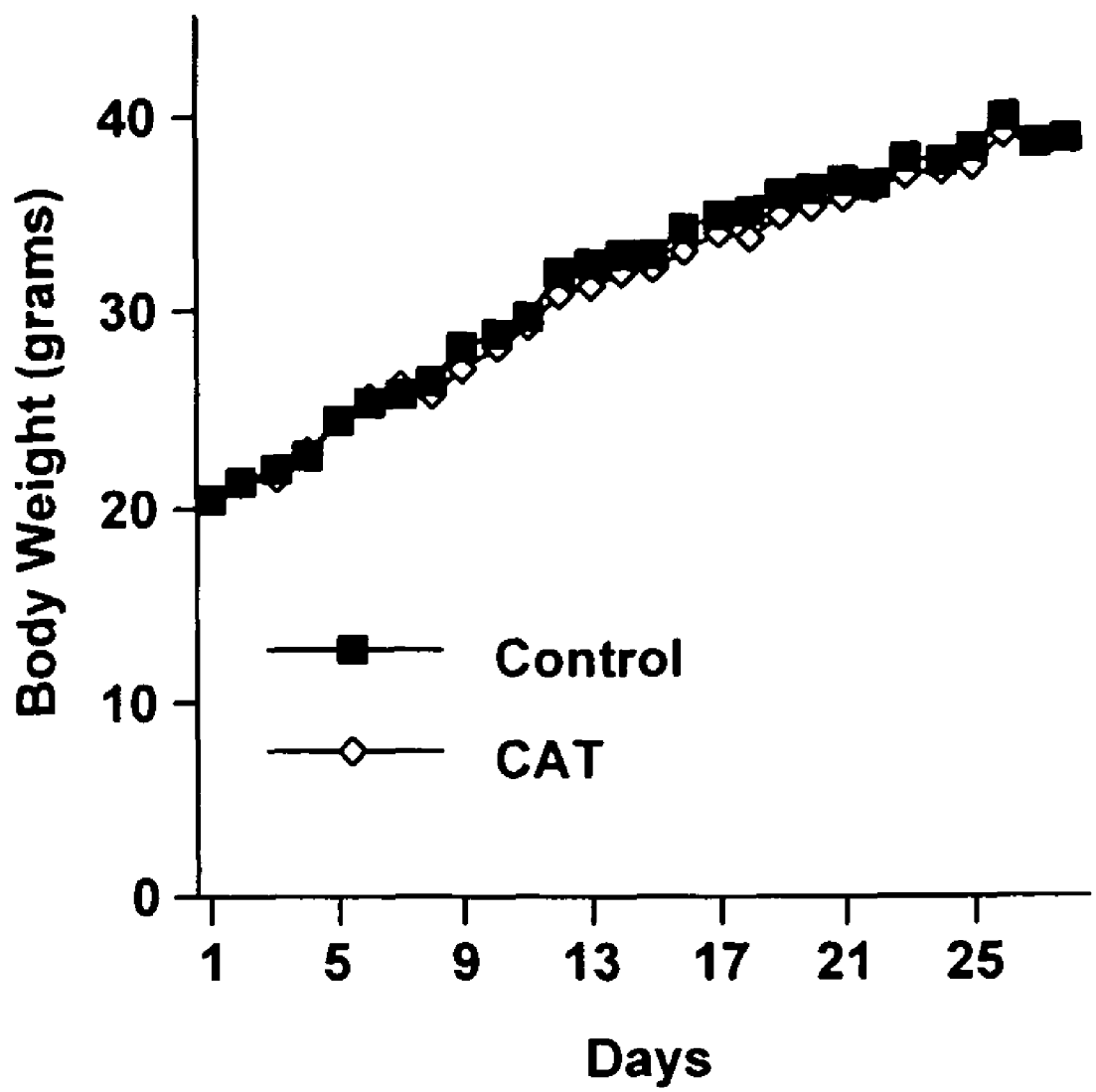
FIG. 4A is a graph illustrating the effect of dietary catalpic acid-supplementation on body weight in Experiment 2.
Figure 4B:
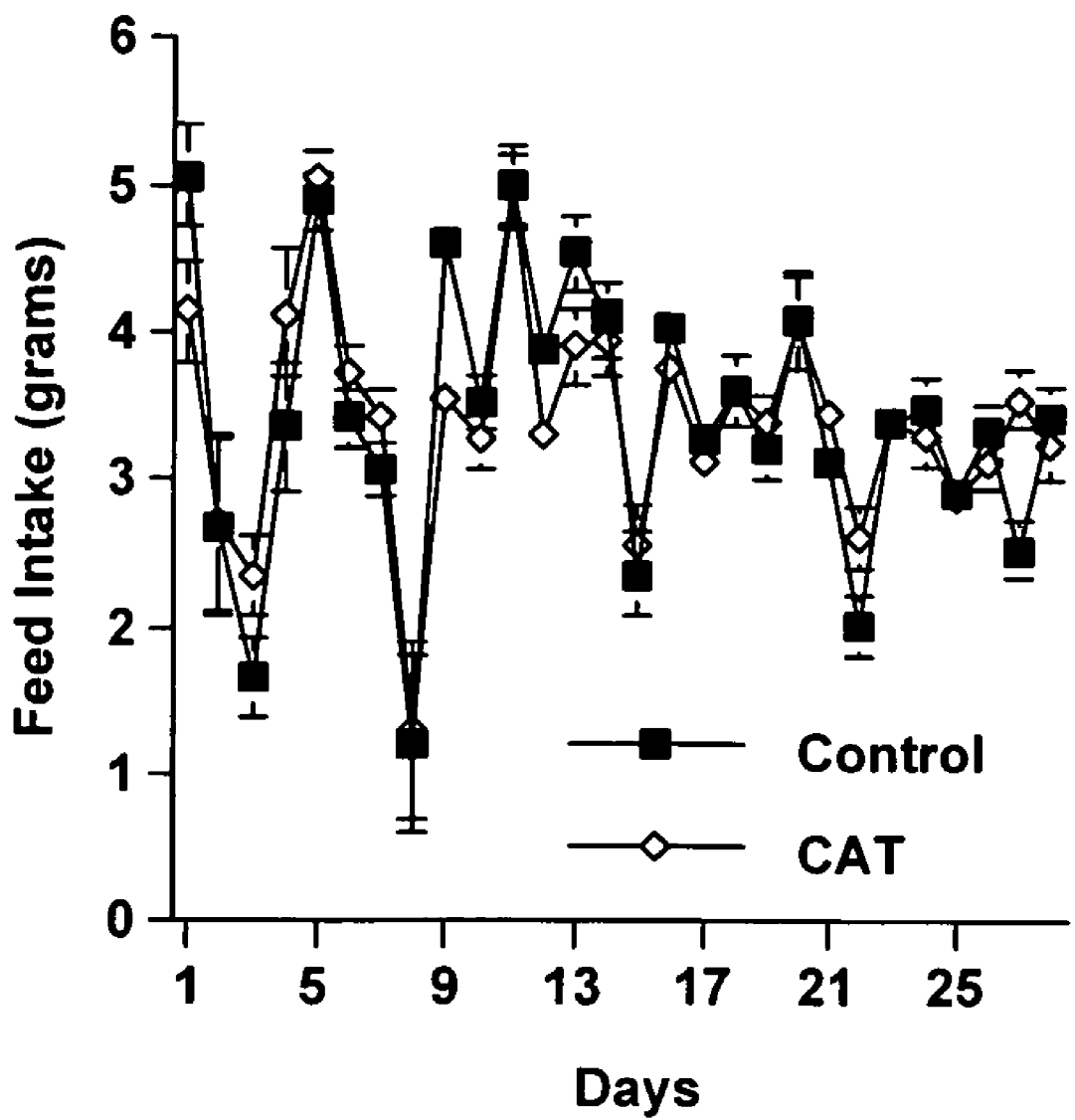
FIG. 4B is a graph illustrating the effect of dietary catalpic acid-supplementation on feed intake in Experiment 2.

FIG. 4A illustrates the effect of dietary catalpic acid-supplementation on body weight in Experiment 2. Mice were weighed on a daily basis. Db/db mice fed either a high fat control diet (filled squares) or a high fat diet supplemented with catalpic acid (1 g/100 g; open rubies). Statistically significant differences (P<0.05) between treatments attributed to the main effects of the diet (*) are indicated. FIG. 4B illustrates the effect of dietary catalpic acid-supplementation on feed intake in Experiment 2. Feeders and food were weighed on a daily basis. Db/db mice fed either a high fat control diet (filled squares) or a high fat diet supplemented with catalpic acid (1 g/100 g; open rubies). Statistically significant differences (P<0.05) between treatments attributed to the main effects of the diet (*) are indicated.

Figure 5:
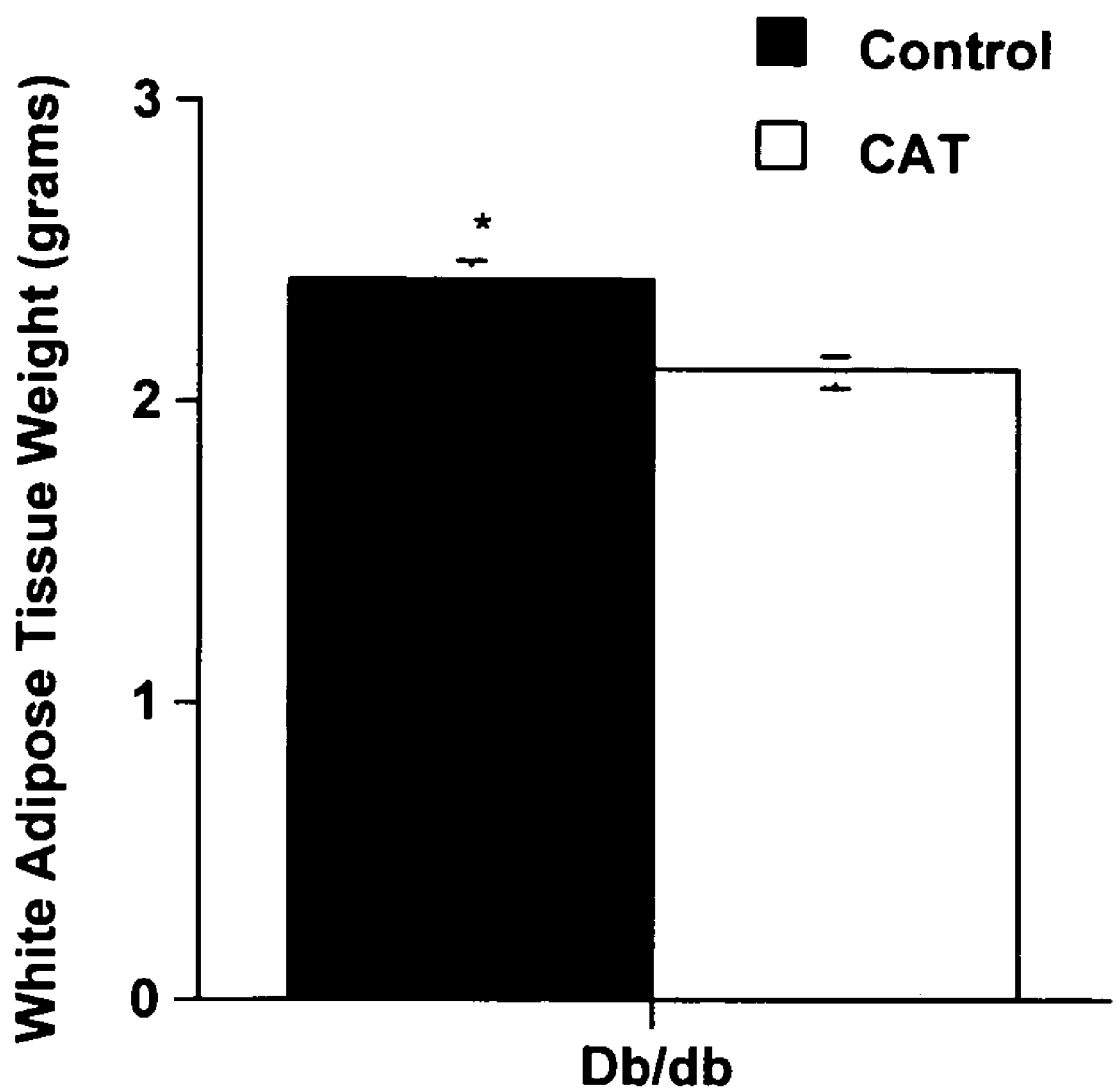
FIG. 5 is a graph illustrating the effect of catalpic acid-supplementation on abdominal white adipose tissue weight on day 28 of Experiment 2.

No differences were found in body weight (FIG. 4A) or feed intake (FIG. 4B). Thus, catalpic acid did not elicit the side effects of current antidiabetic medications. Even though there were no differences in body weight, the WAT weight of mice fed a catalpic acid-supplemented diet was significantly lower than that recovered from mice fed a control diet which is shown in FIG. 5. FIG. 5 illustrates the effect of catalpic acid-supplementation on abdominal white adipose tissue weight on day 28 of Experiment 2. Db/db mice fed either a high fat control diet (filled bar) or a high fat diet supplemented with catalpic acid (1 g/100 g; open bar). Statistically significant differences (P<0.05) between treatments attributed to the main effects of the diet (*) are indicated. The difference in WAT weight between groups attributable to catalpic acid was over 10%.

The glucose tolerance tests are standard methods for evaluating glucose homeostasis in vivo. By using the glucose tolerance test, we previously discovered that glucose tolerance was not different between mice fed regular diets, which did not develop a diabetic phenotype. However, the ability of mice fed a control high fat diet to normalize plasma glucose concentrations was significantly impaired when compared to those fed the high fat diets supplemented with catalpic acid (Experiment 1). Herein, we have confirmed that dietary catalpic acid-supplementation ameliorates the glucose intolerance induced by high fat, diabetogenic diets in mice. In addition, in our previous studies catalpic acid was fed for 78 days, whereas here we observed an effect of dietary catalpic acid after 7 to 28 days of dietary supplementation.

Fasting glucose and insulin concentrations in plasma represent good indicators of insulin sensitivity. Experiment 1 demonstrated that plasma glucose and insulin concentrations were lower in mice fed catalpic-supplemented, high fat diets than in control, high fat diets. Herein, we have confirmed our previous findings. In addition we have demonstrated that catalpic had an immediate effect on insulin concentrations (i.e. 7 days). More specifically, mice fed catalpic acid-supplemented diets were capable of better overcoming the initial metabolic response to the high fat diet. In addition, this initial beneficial effect of dietary catalpic acid-supplementation was maintained throughout the study.

Experiment 3

Objective

The objective of this experiment was to determine the effect of catalpic acid on plasma HDL cholesterol levels, plasma triglyceride levels and expression of fat-burning genes. Specifically, we investigated whether catalpic acid was able to prevent or ameliorate dyslipidemia, characterized by altered triglyceride and cholesterol levels in the plasma, and increase the expression of PPAR alpha, PPAR delta, and PPAR-alpha-responsive genes in adipose tissue.

Methods

Experiment 3 was conducted as described for Experiments 1 and 2 as indicated below except that determination of plasma lipid concentrations and quantitative real-time PCR were performed.

Determination of Plasma Lipid Concentrations

Serum HDL cholesterol concentrations were determined by using a commercial precipitation assay (Wako Diagnostics, Richmond, Va.) per the manufacturer's instructions. The Triglyceride Assay Kit (Sigma) was used to quantify plasma triglyceride concentrations as previously described (Guri et al. 2008).

Quantitative Real-Time PCR

On day 28 or 78 of Experiments 1 and 2, visceral white adipose tissue (WAT) or pancreas samples were collected, stored in RNA later and frozen at −80° C. The dissection of intra-abdominal WAT was performed under magnification. RNA was isolated from WAT and pancreas specimens utilizing RNA isolation columns (Qiagen, Valencia, Calif.) per the manufacturer's instructions. RNA from the WAT was isolated using the Lipid Minikit (Qiagen). RNA was quantified using a μQuant microplate reader (Bio-TEK® Instruments, Inc., Winooski, Vt.). Briefly, total RNA (1 μg) from each sample was used to generate complementary DNA (cDNA) template using the iScript cDNA Synthesis Kit (Bio-Rad, Hercules, Calif.). The total reaction volume was 20 μl. The reaction was incubated as follows in a Tetrad Thermocycler (MJResearch, Waltham, Mass.): 5 minutes at 25° C., 30 minutes at 42° C., 5 minutes at 85° C., hold at 4° C. cDNA products were diluted 1:10 in diethylpyrocarbonate-treated water. Controls were also performed with no RNA template (no template) and omitting the reverse transcriptase enzyme (no RT).

The PCR primer pairs were designed based on previously published sequences (GenBank) using the Oligo 6 primer design software (Molecular Biology Insights, Cascade, Colo.). The PCR primer pair sequences, annealing temperatures, accession numbers and PCR product lengths are outlined in Table 5. PCR was performed on the cDNA with iSCRIPT (BioRad, Hercules, Calif.) using previously described conditions (Hontecillas et al. 2002 and Bassaganya-Riera et al. 2004). Each gene amplicon was purified by using the MiniElute PCR Purification kit (Qiagen). The purified amplicon for each gene was quantified on an agarose gel using a DNA mass ladder. These purified amplicons were further used to optimize the real-time PCR conditions and to generate the standard curves in the real-time PCR assay. Primer concentrations and annealing temperatures were optimized for the iCycler iQ System (Bio-Rad) for each set of primers using the system's gradient protocol. PCR efficiencies were maintained at 92 to 105% for each primer set during optimization and also during the real-time PCR of sample cDNA.

unknown starting quantity of cDNA on a 96-well plate. For each gene, the results were calculated as starting quantity of cDNA (picograms) per microgram of RNA.

Statistics

Data were analyzed by analysis of variance (ANOVA). The ANOVA was performed by using the general linear model procedure of SAS (SAS Institute Inc., Cary, N.C.) as previously described (Bassaganya-Riera 2004). Data were analyzed as a completely randomized design. Differences with probability value (P<0.05) were considered significant. The statistical model for both experiments was: $Y_{ijk}=\mu+Diet+error$.

Results

The cholesterol contained in high-density lipoprotein (HDL), as opposed to that contained in low-density lipoprotein (LDL) or very low-density lipoprotein (VLDL), represents the cholesterol that is targeted for excretion from the body and thus represents the "good cholesterol" found in the bloodstream. As such, a nutraceutical that increases HDL levels is viewed as therapeutic for hypercholesterolemia, car-

TABLE 5

Oligonucleotide Sequences for Quantitative Real-Time PCR[1,2].

| Primer | Sequence | Length (bp) | Accession No. | AT (° C.) | SEQ. ID. NOS. |
|---|---|---|---|---|---|
| PPAR alphaF | 5'TGGGGATGAAGAGGGCTGAG3' | 143 | NM_011144 | 57 | SEQ. ID. NO: 1 |
| PPAR alphaR | 5'GGGGACTGCCGTTGTCTGT3' | | | | SEQ. ID. NO: 2 |
| PPAR deltaF | 5'ACAGTGACCTGGCGCTCTTC3' | 96 | U10375 | 57 | SEQ. ID. NO: 3 |
| PPAR deltaR | 5'TGGTGTCCTGGATGGCTTCT3' | | | | SEQ. ID. NO: 4 |
| PPAR gammaF | 5'CAGGCTTGCTGAACGTGAAG3' | 117 | NM_011146 | 57 | SEQ. ID. NO: 5 |
| PPAR gammaR | 5'GGAGCACCTTGGCGAACA3' | | | | SEQ. ID. NO: 6 |
| SCD1F | 5'TGGGCAAGTGCTAATGGACC3' | 133 | NM_009127 | 55.5 | SEQ. ID. NO: 7 |
| SCD1R | 5'GGCCCTGGACTGTGTGACA3' | | | | SEQ. ID. NO: 8 |
| ECHF | 5'CTTCACTGTAAGGGCAGGTG3' | 122 | NM_053119 | 55.6 | SEQ. ID. NO: 9 |
| ECHR | 5'CTTGAGTTGGGAATCAGCAG3' | | | | SEQ. ID. NO: 10 |
| b-actinF | 5'CCCAGGCATTGCTGACAGG3' | 141 | X03672 | 57 | SEQ. ID. NO: 11 |
| b-actinR | 5'TGGAAGGTGGACAGTGAGGC3' | | | | SEQ. ID. NO: 12 |

[1]F, forward; R, reverse. PCR primer pairs were designed for an optimal annealing temperature (AT) between 52.5 and 58.2° C. and product length shorter than 171 base pairs.
[2]When plotting threshold cycle versus log starting quantity (pg), standard curves had slopes between −3.1 and −3.7; PCR efficiencies between 92 and 105 and $R^2$ above 0.98.

Messenger RNA (mRNA) expression of peroxisome proliferator-activated receptor (PPAR) gamma, PPAR alpha, and PPAR delta was determined in adipose tissue. Based on the patterns of expression of the nuclear receptors in each tissue, the expression of a relevant panel of responsive genes was evaluated by quantitative real-time PCR. We found that WAT PPAR alpha expression was increased by the CAT diet supplementation in WAT. Therefore, we also examined the expression of four PPAR alpha-responsive genes in WAT, including acyl-coenzyme A dehydrogenase (ACDH), stearoyl-coenzyme A desaturase (SCD1), enoyl-coenzyme A hydratase (ECH) and carnitine palmitoyl transferase-1 (Cpt-1).

Transcript expression was examined by real-time, quantitative PCR by using an iCycler iQ System and the iQ SYBR Green Supermix (Bio-Rad). Real-time PCR was used to measure the starting amount of nucleic acid by assaying each diovascular disease, and the Metabolic Syndrome in general. In contrast, high triglyceride levels are deleterious, and an agent that lowers plasma triglycerides is therapeutic. We found that CAT increased plasma HDL cholesterol concentrations and decreased plasma triglyceride levels during high-fat feeding. Consistent with this effect, we also found that CAT increased expression of genes involved in fat oxidation.

PPAR alpha and PPAR delta are transcription factors that promote the expression of lipid metabolism genes. SCD1 and ECH are both targets of PPAR alpha and favor oxidation (i.e., burning) of fat. We used real-time PCR to quantify the expression of PPAR alpha, gamma and delta in WAT from wild-type mice fed high-fat diets, as described in Experiment 1. Our data demonstrate that PPAR alpha was upregulated in WAT of mice fed CAT-supplemented diets (Table 6). We next examined the effect of dietary CAT on expression of PPAR alpha-responsive genes in WAT. CAT feeding induced an upregulation of steroyl coenzyme A desaturase (SCD1) and enoyl coenzyme A hydratase (ECH) in wild-type mice fed high-fat diets (Table 6). We then quantified the expression of PPAR alpha, SCD1 and ECH in obese db/db mice fed control and CAT-supplemented diets, as described in Experiment 2. In line with results from Experiment 1, db/db mice fed CAT upregulated PPAR alpha and SCD1 but not ECH (Table 7).

Figure 6A:
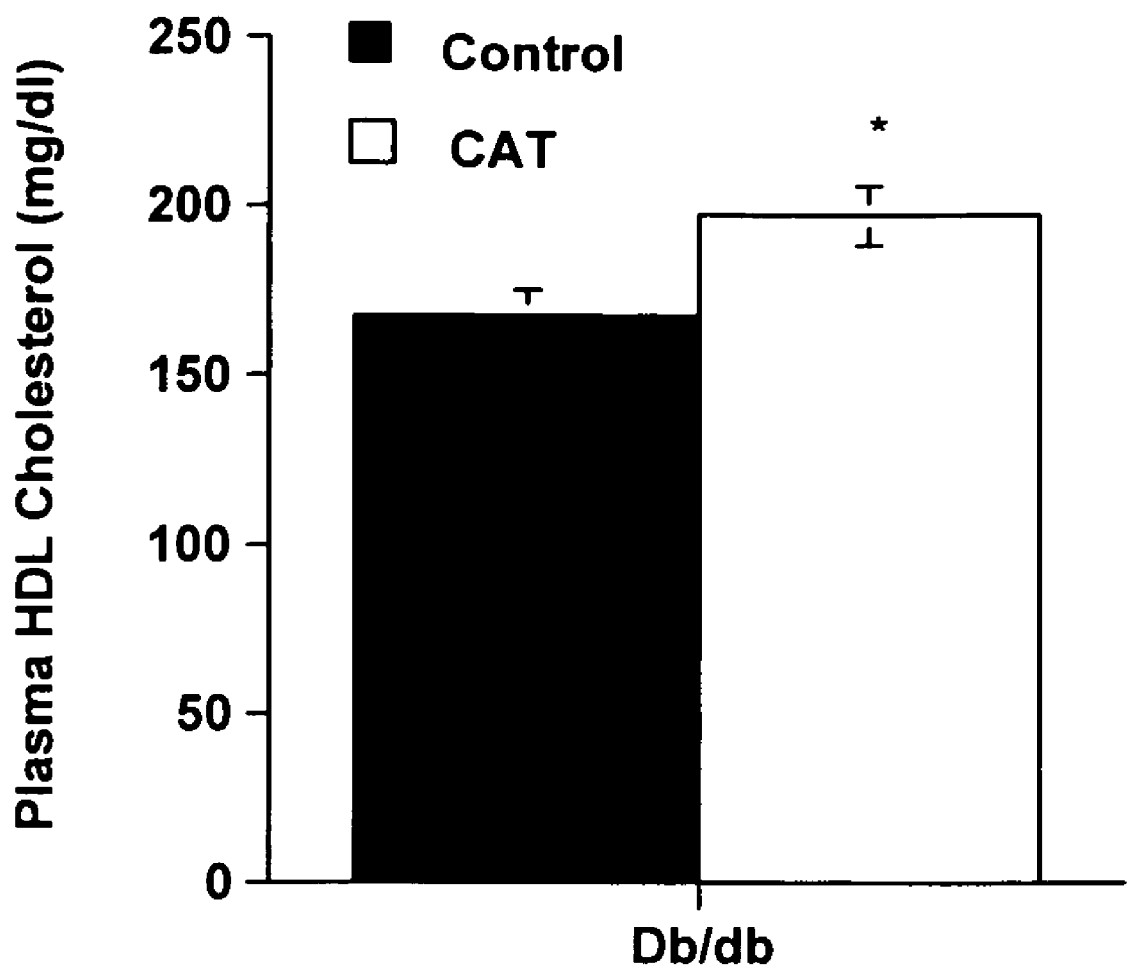
FIG. 6A is a graph illustrating the effect of catalpic acid-supplementation on plasma HDL cholesterol in Experiment 3.
Figure 6B:
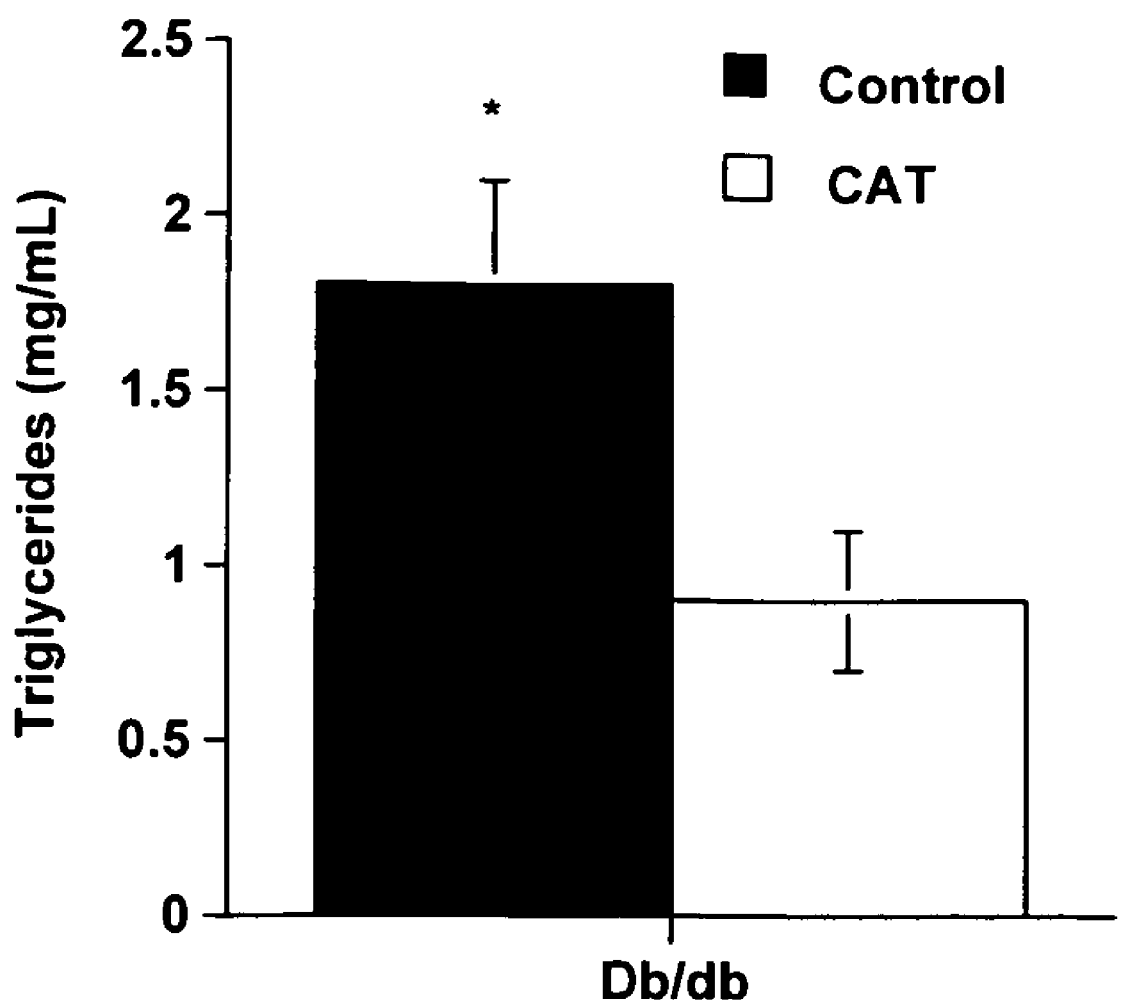
FIG. 6B is a graph illustrating the effect of catalpic acid-supplementation on plasma triglycerides in Experiment 3.

HDL cholesterol concentrations were greater in obese mice fed CAT-supplemented high-fat diets than in those fed control high-fat diets (FIG. 6A). Conversely, plasma triglyceride concentrations were lower in mice fed CAT-supplemented high-fat diets than in mice fed the control high-fat diets (FIG. 6B).

TABLE 6

Effect of dietary catalpic acid (CAT)-supplementation of C57BL/6J wild-type mice for 78 days on the mRNA expression of peroxisome proliferator-activated receptor a (PPAR alpha) and its responsive genes in white adipose tissue[1,2].

| Transcript | Control | CAT | SEM[3] | P value |
|---|---|---|---|---|
| PPAR gamma | 0.078 | 0.074 | 0.02 | 0.88 |
| PPAR delta | 0.004 | 0.007 | 0.001 | 0.27 |
| PPAR alpha | $0.0007^b$ | $0.005^a$ | 0.001 | 0.03 |
| Stearoyl CoA Desaturase | $0.068^b$ | $0.130^a$ | 0.02 | 0.05 |
| Enoyl CoA Hydratase | $0.002^b$ | $0.0039^a$ | 0.0003 | 0.05 |

[1]Data are presented as picograms of starting cDNA per microgram of white adipose tissue total RNA.
[2]Least squares means values (n = 10) in a row for a particular tissue with different superscripts are significantly different (P < 0.05).
[3]Pooled standard error of the least square means.

TABLE 7

Effect of dietary catalpic acid (CAT)-supplementation of db/db mice for 28 days on the mRNA expression of peroxisome proliferator-activated receptor a (PPARa) and its responsive genes in white adipose tissue[1,2].

| Transcript | Control | CAT | SEM[3] | P value |
|---|---|---|---|---|
| PPAR alpha | $0.0020^b$ | $0.0052^a$ | 0.0006 | 0.0054 |
| Stearoyl CoA Desaturase | $0.039^b$ | $0.095^a$ | 0.015 | 0.02 |
| Enoyl CoA Hydratase | 0.0028 | 0.0024 | 0.0003 | 0.57 |

[1]Data are presented as picograms of starting cDNA per microgram of white adipose tissue total RNA.
[2]Least squares means values (n = 10) in a row for a particular tissue with different superscripts are significantly different (P < 0.05).
[3]Pooled standard error of the least square means.

Conclusions from Experiments 1-3 and Further Data

Our data show that dietary CAT-supplementation for 78 days improved fasting glucose and insulin concentrations, enhanced the ability of mice to normalize plasma glucose concentrations following a glucose tolerance test and decreased the accumulation of abdominal WAT in a model of diet-induced obesity (Experiment 1). Similar findings were observed in genetically obese db/db mice fed CAT for 30 days (Experiment 2). In addition, CAT increased HDL cholesterol while decreasing triglyceride levels in plasma (Experiment 3). The effects of CAT on HDL and triglyceride levels is not only preventative and therapeutic for dyslipidemia but is also preventative and therapeutic for cardiovascular disease because treatment of dyslipidemia reduces the risk of cardiovascular disease (Ginsberg 2003).

Based on the purported effects of CAT on glucose, insulin and lipid homeostasis and because PPARs are central modulators of lipid and carbohydrate metabolism we examined the expression of PPAR alpha, gamma and delta in WAT. Our data demonstrated that PPAR alpha and PPAR alpha-responsive genes are upregulated in WAT of mice administered CAT, whereas PPAR gamma and delta expression are not significantly affected by CAT in WAT. These data show that the changes in plasma lipid levels were associated with an upregulation of PPAR alpha and its responsive genes (e.g., SCD1 and ECH) in WAT of mice fed CAT-supplemented diets. These data suggest that the metabolic effects of CAT on glucose and lipid metabolism may be mediated through a PPAR alpha-dependent mechanism.

The activation of PPAR alpha, enrichment of HDL and lowering of plasma triglyceride concentrations has been a consistent finding observed following administration of a class of PPAR alpha agonistic drugs known as fibrates (Hossain et al. 2008). This class of lipid-lowering drugs has played a major role in the treatment of hyperlipidemia for more than two decades. However, fibrates are also associated with significant side effects including increased risk for myopathy, cholelithiasis and venous thrombosis (Davidson et al. 2007). Our data suggest that CAT may modulate lipid and glucose homeostasis by acting through a PPAR alpha-dependent pathway.

The effects of CAT on glucose homeostasis could be interpreted as dependent on PPAR gamma or PPAR alpha activity because their synthetic agonists elicit antidiabetic actions. Specifically, glitazones such as rosiglitazone (Avandia) are known for their insulin-sensitizing effects (Knowler et al. 2005) and fibrates such as fenofibrate (Tricor, Triglide, Lofibra) are known primarily for both their lipid-lowering properties but also for their ability to improve glycemic control (Tsunoda et al. 2008). It is, however, the lipid-lowering actions of CAT that are in line with the PPAR alpha agonistic actions of fibrates (Remick et al. 2008). Of note, fibrates increase HDL cholesterol through a PPAR alpha-induced transcriptional activation of liver X receptor alpha, a nuclear receptor that increases reverse cholesterol transport through promotion of the ATP-binding cassette transporters ABCA-1 and ABCG-1 (Chawla et al. 2001, Walczak et al. 2002, and Chinetti et al. 2001).

Another important finding in our study is that dietary CAT also decreases plasma insulin concentrations. In this regard, high-fat diets contain high concentrations of saturated fatty acids which are known to stimulate the secretory activity of insulin-producing beta-cells in the pancreas and cause lipotoxicity at elevated concentrations. Interestingly, a recent study has demonstrated that PPAR alpha/RXR agonists induce beta-cell protection against palmitate toxicity (Hellemans et al. 2007). Thus, activation of beta-cell PPAR alpha by CAT would also represent a likely explanation for the decreased plasma insulin concentrations observed in CAT-fed mice. However, pancreatic concentrations of PPAR alpha and its responsive genes were unchanged, but PPAR delta was upregulated in the pancreas of CAT-fed mice (0.028 versus 0.069; P<0.04). The mechanism by which PPAR alpha is believed to elicit its cytoprotective actions in the pancreas is by favoring beta-oxidation of fatty acids. Therefore, if pancreatic PPAR alpha remains unaffected and PPAR delta is upregulated by CAT, it would be possible that PPAR delta-mediated beta-oxidation is increased by CAT, resulting in decreased fatty acid-induced insulin secretion.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

BIBLIOGRAPHY

Bassaganya-Riera, J., K. Reynolds, et al. (2004). "Activation of PPAR gamma and delta by conjugated linoleic acid mediates protection from experimental inflammatory bowel disease." *Gastroenterology* 127(3): 777-91.

Center for Disease Control (2004). National diabetes fact sheet: general information and national estimates on diabetes in the United States, 2003. Atlanta, U.S. Department of Health and Human Services, Centers for Disease control and Prevention.

Chawla, A., W. A. Boisvert, et al. (2001). "A PPAR gamma-LXR-ABCA1 pathway in macrophages is involved in cholesterol efflux and atherogenesis." *Mol Cell* 7: 161-71.

Chinetti, G., S. Lestavel, et al. (2001). "PPAR-alpha and PPAR-gamma activators induce cholesterol removal from human macrophage foam cells through stimulation of the ABCA1 pathway." *Nature Medicine* 7: 53-8.

Davidson, M. H., A. Armani, et al. (2007). "Safety considerations with fibrate therapy." *Am J Cardiol* 99: 3C-18C.

Ginsberg, H. N. (2003). "Treatment for patients with the metabolic syndrome." *Am J Cardiol* 91(7A): 29E-39E.

Guri, A. J., R. Hontecillas, et al. (2008). "Loss of PPAR gamma in immune cells impairs the ability of abscisic acid to improve insulin sensitivity by suppressing monocyte chemoattractant protein-1 expression and macrophage infiltration into white adipose tissue." *J Nutr Biochem* 19: 216-28.

Hellemans, K., K. Kerckhofs, et al. (2007). "Peroxisome proliferator-activated receptor alpha-retinoid X receptor agonists induce beta-cell protection against palmitate toxicity." *Febs J* 274: 6094-105.

Hossain, M. A., M. Tsujita, et al. (2008). "Effects of fibrate drugs on expression of ABCA1 and HDL biogenesis in hepatocytes." *J Cardiovasc Pharmacol* 51: 258-66.

Hontecillas, R., M. J. Wannemeulher, et al. (2002). "Nutritional regulation of porcine bacterial-induced colitis by conjugated linoleic acid." *J Nutr* 132: 2019-27.

Knowler, W. C., R. F. Hamman, et al. (2005). "Prevention of type 2 diabetes with troglitazone in the Diabetes Prevention Program." *Diabetes* 54: 1150-6.

Remick, J., H. Weintraub, et al. (2008). "Fibrate therapy: an update." *Cardiol Rev* 16: 129-41.

Tsunoda, M., N. Kobayashi, et al. (2008). "A novel PPAR{alpha} agonist ameliorates insulin resistance in dogs fed a high-fat diet." *Am J Physiol Endocrinol Metab* 294: E833-40.

Walczak, R. & Tontonoz, P. (2002) "PPARadigms and PPARadoxes: expanding roles for PPARgamma in the control of lipid metabolism." *J Lipid Res* 43: 177-86.

Wang, Y. X., C. H. Lee, et al. (2003). "Peroxisome-proliferator-activated receptor delta activates fat metabolism to prevent obesity." *Cell* 113(2): 159-70.

U.S. Pat. No. 6,451,439 to Okamoto
U.S. Pat. No. 6,593,514 to Cahoon
U.S. Patent Application 20030126640 to Cahoon
U.S. Patent Application 20020045232 to Qiu

What is claimed is:

1. A method of increasing plasma HDL, decreasing plasma triglycerides, or increasing plasma HDL and decreasing plasma triglycerides in an animal, comprising administering an amount of a compound selected from the group consisting of catalpic acid, glyceride esters thereof, pharmaceutically-suitable salts thereof, and combinations thereof, wherein the amount of the compound is effective to increase plasma HDL, decrease plasma triglycerides, or increase plasma HDL and decrease plasma triglycerides.

2. The method of claim 1, comprising administering a free form of catalpic acid.

3. The method of claim 1, comprising administering the compound orally in combination with a pharmaceutically suitable oral carrier.

4. The method of claim 3, comprising administering the compound orally in a solid, semi-solid, liquid or gas state.

5. The method of claim 1, comprising administering the compound parenterally.

6. The method of claim 1, wherein the amount of the compound is between about 0.001 g and about 20 g per kg body weight per day.

7. The method of claim 1, wherein the amount of the compound is between about 0.1 g and about 10 g per kg body weight per day.

8. The method of claim 1, wherein the amount is effective to increase PPAR alpha in the animal.

9. The method of claim 8, comprising administering a free form of catalpic acid.

10. The method of claim 8, comprising administering the compound orally in combination with a pharmaceutically suitable oral carrier.

11. The method of claim 8, comprising administering the compound parenterally.

12. The method of claim 8, wherein the effective amount of the compound is between about 0.001 g to about 20 g per kg body weight per day.

13. The method of claim 1 comprising administering a glyceride form of catalpic acid.

14. The method of claim 8 comprising administering a glyceride form of catalpic acid.

15. The method of claim 8, wherein the amount is effective to increase PPAR alpha in white adipose tissue in the animal.

16. The method of claim 8, wherein the amount of the compound is between about 0.1 g and about 10 g per kg body weight per day.

* * * * *